(12) United States Patent
Kagechika

(10) Patent No.: US 7,084,133 B2
(45) Date of Patent: Aug. 1, 2006

(54) DICARBA-CLOSO-DODECABORANE DERIVATIVES

(76) Inventor: Hiroyuki Kagechika, 2-39-6, Oizumi-machi, Nerima-ku, Tokyo 178-0062 (JP)

( * ) Notice: Subject to any disclaimer, the term of this patent is extended or adjusted under 35 U.S.C. 154(b) by 0 days.

(21) Appl. No.: 10/470,268

(22) PCT Filed: Feb. 8, 2002

(86) PCT No.: PCT/JP02/01078

§ 371 (c)(1), (2), (4) Date: Jan. 20, 2004

(87) PCT Pub. No.: WO02/064601

PCT Pub. Date: Aug. 22, 2002

(65) Prior Publication Data

US 2004/0102417 A1    May 27, 2004

(30) Foreign Application Priority Data

Feb. 9, 2001    (JP) .............................. 2001-033674

(51) Int. Cl.
*A61K 31/69*    (2006.01)
(52) U.S. Cl. ........................................... 514/64; 568/5
(58) Field of Classification Search ............ 568/5; 514/64
See application file for complete search history.

(56) References Cited

U.S. PATENT DOCUMENTS 3,166,597 A * 1/1965 Ager, Jr. et al. ................. 568/5
3,258,479 A    6/1966 Alexander et al.
H000786 H * 6/1990 Adolph et al. ................. 528/4
2003/0191342 A1   10/2003 Kagechika et al.

FOREIGN PATENT DOCUMENTS

EP    1145718    10/2001
JP    61-76440   4/1986
WO    00/43016   7/2000

OTHER PUBLICATIONS

Ingham et al., *Chemical Abstracts*, vol. 76, No. 9, 1972, p. 382, abstract No. 4632.
Fox et al., Transmission of Electronic Effects by Icosahedral Carboranes; Skeletal Carbon—13 Chemical Shifts and Ultraviolet-Visible Spectra of Substitute Aryl-*p*-carboranes (1,12-dicarba-*closo*-dodecaboranes), *J. Chem. Soc. Dalton Trans.*, pp. 401-411, 1998.
Zakharkin et al., "Electrophilic and Nucleophilic Constants of o- and m-carboran-1-yl and o-carboran-3-yl groups," English translation of *Zh. Obshch. Khim.*, vol. 41, pp. 1516-1520, 1971.
English language Abstract of JP 61-76440.

* cited by examiner

*Primary Examiner*—Michael L. Shippen

(57) ABSTRACT

A compound represented by the following general formula (I), wherein $R^1$ represents a hydroxy-substituted alkyl group, a hydroxy-substituted alkenyl group, a hydroxy-substituted arylalkyl group (said arylalkyl group may have a substituent on the aryl ring), or a hydroxy-substituted arylalkenyl group (said arylalkenyl group may have a substituent on the aryl ring); X represents a dicarba-closo-dodecaborane-diyl group; $R^2$ represents a hydroxy-substituted alkyl group or a hydroxy-substituted alkoxyalkyl group, or a salt thereof, which is useful as an agent exerting vitamin D actions or an agent for enhancing vitamin D actions $$R^1\text{—}X\text{—}R^2.$$

18 Claims, No Drawings

DICARBA-CLOSO-DODECABORANE DERIVATIVES

TECHNICAL FIELD

The present invention relates to a novel dicarba-closo-dodecaborane derivative. The present invention also relates to a medicament comprising said dicarba-closo-dodecaborane derivative as an active ingredient.

BACKGROUND ART

Dicarba-closo-dodecaborane (hereinafter abbreviated as "carborane" in the specification) is an icosahedral cluster containing two carbon atoms and ten boron atoms in which both atoms are hexacordinated. In caboranes, depending on the position of the carbon atoms in the cluster, 3 kinds of isomers exist, i.e., 1,2-dicarba-closo-dodecarobane (ortho-carborane), 1,7-dicarba-closo-dodecaborane (meta-carborane), and 1,12-dicarba-closo-dodecaborane (para-carborane). These structures are unique among boron compounds, namely they are characterized to have very high thermal stability and hydrophobicity comparable to hydrocarbons.

A major utility of compounds composed of a carborane so far has been an application to [10]Boron-Neutron Capture Therapy (BNCT). [10]Boron-Neutron Capture Therapy has been developed as a therapy mainly to glioma and melanoma. When [10]B atom is irradiated with thermal neutron (slow neutron), an α ray with 2.4 MeV energy is emitted and the atom is decomposed to [7]Li and [4]He. The range of α ray is about 10 μm which corresponds to a diameter of cells. Therefore, effects are expected that only cells in which [10]B atoms are uptaken are destroyed and other cells are not damaged. For the development of BNCT, it is important how to have cancer cells selectively uptake [10]B atoms in a concentration capable of destroying cells with neutron radiation. For that purpose, ortho-carborane skeleton has been utilized which has low toxicity and a high [10]B atom content, and is easy to be synthesized. Moreover, nucleic acid precursors, amino acids, and porphyrins which contain ortho-carboranes have been synthesized and subjected to evaluation.

Recently, physiologically active compounds having a carborane skeleton as a pharmacophore have been reported (International Patent Publication WO00/43016). These compounds have physiological activities of retinoid actions, anti-estrogen action and the like, and they are useful for the treatment of leukemia and the like.

DISCLOSURE OF THE INVENTION

The inventor of the present invention conducted various studies to provide a physiologically active compound having a carborane skeleton as a pharmacophore. As a result, it was found that the compounds having a dicarba-closo-dodecaborane structure represented by the following general formula (I) had vitamin D-like actions, or the compounds markedly enhanced the actions of vitamin D, even when the compounds, per se, had no vitamin D-like action. The present invention was achieved on the basis of the aforementioned findings.

The present invention thus provides a compound represented by the following general formula (I):

$$R^1—X—R^2$$

wherein $R^1$ represents a hydroxy-substituted alkyl group, a hydroxy-substituted alkenyl group, a hydroxy-substituted arylalkyl group (said arylalkyl group may have a substituent on the aryl ring), or a hydroxy-substituted arylalkenyl group (said arylalkenyl group may have a substituent on the aryl ring); X represents a dicarba-closo-dodecaborane-diyl group; $R^2$ represents a hydroxy-substituted alkyl group or a hydroxy-substituted alkoxyalkyl group, or a salt thereof.

According to a preferred embodiment of the present invention, there is provided the aforementioned compound or a salt thereof, wherein the hydroxy-substituted alkenyl group represented by $R^1$ is a group represented by the following formula (a):

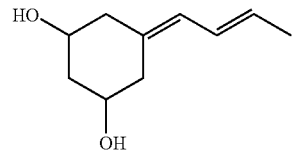

From another aspect, the present invention provides a medicament comprising the compound represented by the aforementioned formula (I) or a physiologically acceptable salt thereof as an active ingredient. This medicament can be used as an agent exerting vitamin D actions or an agent for enhancing vitamin D actions. The present invention further provides use of the compound represented by the aforementioned formula (I) or a physiologically acceptable salt thereof for manufacture of the aforementioned medicament, and a method for prophylactic and/or therapeutic treatment of a disease involving vitamin D, such as vitamin D deficiency, which comprises the step of administering a prophylactically and/or therapeutically effective amount of the compound represented by the aforementioned formula (I) or a physiologically acceptable salt thereof to a mammal including human. Moreover, the present invention provides an agent exerting vitamin D actions or an agent for enhancing vitamin D actions, which comprises a compound containing the dicarba-closo-dodecaborane structure. As the compound containing the dicarba-closo-dodecaborane structure, the compounds represented by the aforementioned formula (I) are preferred.

BEST MODE FOR CARRYING OUT THE INVENTION 1,2-Dicarba-closo-dodecaborane (ortho-carborane) is the compound described on the upper side of the following formulas. It contains ten boron atoms (represented by "B" in the formulas) having hydrogen atom and two carbon atoms (represented by "C" in the formulas) having hydrogen atom. The 1,2-dicarba-closo-dodecaborane-1,2-diyl group is a group corresponding to a residue formed by eliminating the hydrogen atoms on two of carbon atoms on the carborane ring of the compound of the formula. As dicarba-closo-dodecaborane, 1,7-dicarba-closo-dodecaborane (meta-carborane) and 1,12-dicarba-closo-dodecaborane (para-carborane) are also known. These compounds can form 1,7-dicarba-closo-dodecaborane-1,7-diyl group and 1,12-dicarba-closo-dodecaborane-1,12-diyl group, like the ortho-carborane. $R^1$ and $R^2$ can substitute also on boron atoms.

The term "dicarba-closo-dodecaborane-diyl group" used in the specification includes the residues of three kinds of isomers of dicarba-closo-dodecaborane. The carbon atoms and boron atoms to which $R^1$ and $R^2$ do not bind may independently have a substituent. As an example, 1,12- dicarba-closo-dodecaborane (para-carborane) in which methyl groups substitute on all of the ten boron atoms ($R^1$ and $R^2$ bind to the 1-position and 12-position, respectively) is shown on the lower side of the following formulas.

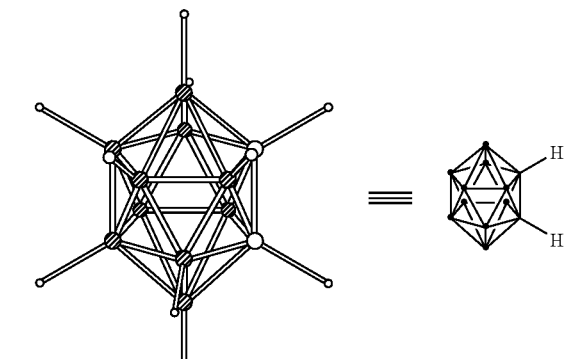

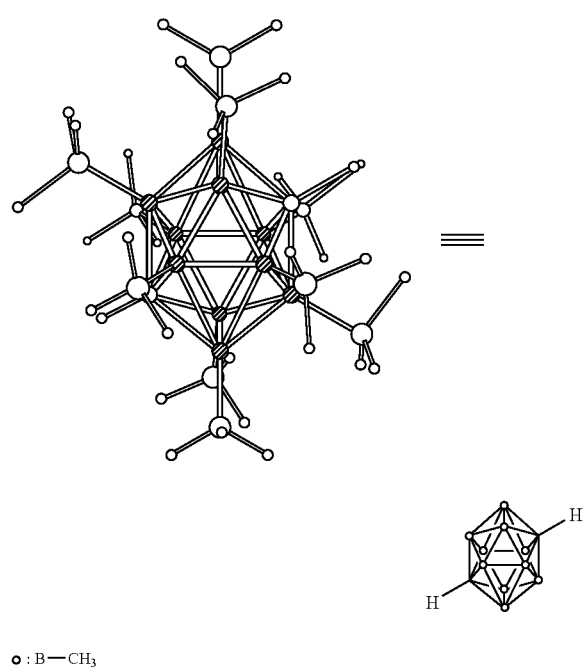

o : B—CH$_3$

In the specification, the alkyl group, alkenyl group, and alkoxyalkyl group constituting a main chain of the hydroxy-substituted alkyl group, hydroxy-substituted alkenyl group, hydroxy-substituted arylalkyl group, hydroxy-substituted arylalkenyl group or hydroxy-substituted alkoxyalkyl group may be linear, branched or cyclic, or may consist of a combination of these. The carbon number of these groups is about 1 to 16, preferably 1 to 12, more preferably 1 to 8. The number of double bonds included in the alkenyl group is not particularly limited. The alkenyl group may contain two or more of conjugated or non-conjugated double bonds. The alkenyl group may preferably contain two of conjugated double bonds. The alkoxyalkyl group may further contain one or two oxygen atoms in the main chain, and the group is meant to encompass an alkoxyalkoxyalkyl group and an alkoxyalkoxyalkoxyalkyl group.

The number and substituting positions of hydroxyl groups present in the hydroxy-substituted alkyl group, hydroxy-substituted alkenyl group, hydroxy-substituted arylalkyl group, hydroxy-substituted arylalkenyl group, or hydroxy-substituted alkoxyalkyl group are not particularly limited. For example, the aforementioned groups preferably have one or two hydroxyl groups. When the groups have one hydroxyl group, they may preferably be secondary or tertiary hydroxyl group. When the group have two hydroxyl groups, one or two hydroxyl groups may preferably be secondary hydroxyl groups. A combination of secondary hydroxyl group and tertiary hydroxyl group is also preferred.

The type of the aryl group constituting the hydroxy-substituted arylalkyl group or hydroxy-substituted arylalkenyl group is not particularly limited. For example, phenyl group, naphthyl group and the like are preferred. One or more substituents may exist on the ring of the aryl group, and the types, substituting positions, and number of such substituents are not particularly limited. Examples of the substituents include hydroxyl group, a halogen atom (which may be any of fluorine atom, chlorine atom, bromine atom and iodine atom), an alkyl group, an alkoxyl group and the like. $R^1$ is preferably a group represented by the aforementioned formula (a) or a monohydroxyalkyl group, more preferably a group represented by following formula (b):

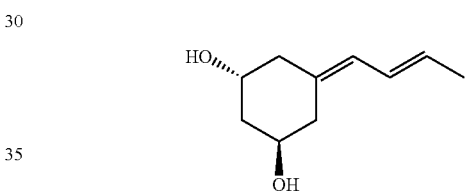

$R^2$ is preferably a monohydroxyalkyl group, a dihydroxyalkoxyalkyl group or the like.

The dicarba-closo-dodecaborane-diyl group may not have a substituent other than $R^1$ and $R^2$. Alternatively, the group may have one or more substituents other than $R^1$ and $R^2$. In the latter case, the substituting positions of substituents are not particularly limited, and one or more substituents may exist on one carbon atom of the carborane ring and/or a part or all of the boron atoms. Examples of the substituents include, for example, substituents selected from the group consisting of a lower alkyl group, a lower alkenyl group, carboxyl group, a lower alkoxycarbonyl group, amino group, hydroxyl group, a lower hydroxyalkyl group, a mono- or di-(lower alkyl)carbamoyl-substituted alkyl group, a lower alkanoyl group, an aryl group which may be substituted and a lower aralkyl group which may be substituted, and the like. For example, a carborane ring all of which boron atoms are alkylated, for example, methylated may be used.

Typical compounds among the compounds of the present invention will be shown below. However, the scope of the present invention is not limited to the following examples. In the table, Me represents methyl group, Et represents ethyl group, Pr represents propyl group, Bu represents butyl group, Ph represents phenyl group, and the dicarba-closo-dodecaborane-diyl group is schematically represented at the center of the formulas.

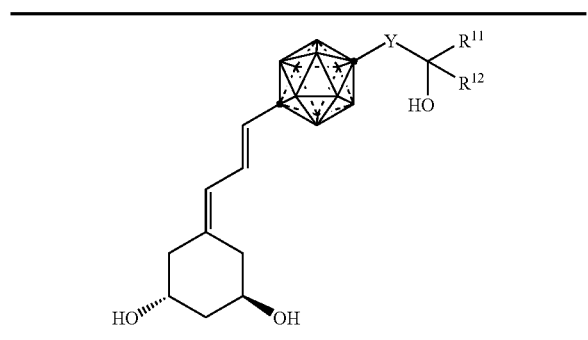

| | Y | R¹¹ | R¹² |
|---|---|---|---|
| 1 | —(CH$_2$)$_2$— | Me | Me |
| 2 | —(CH$_2$)$_3$— | Me | Me |
| 3 | —(CH$_2$)$_4$— | Me | Me |
| 4 | —CH$_2$O(CH$_2$)$_2$— | Me | Me |
| 5 | —CH$_2$O(CH$_2$)$_3$— | Me | Me |
| 6 | —CH$_2$O(CH$_2$)$_4$— | Me | Me |
| 7 | —CH$_2$OCH$_2$— | H | Et |
| 8 | —CH$_2$OCH$_2$— | H | tertBu |
| 9 | —CH$_2$OCH$_2$— | Et | Et |
| 10 | —CH$_2$OCH$_2$— | isoPr | isoPr |
| 11 | —CH$_2$OCH$_2$— | nBu | nBu |
| 12 | —CH$_2$OCH$_2$— | Ph | Ph |

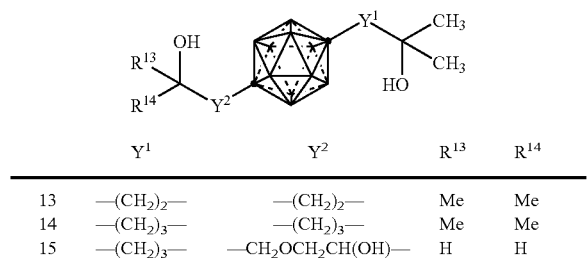

| | Y¹ | Y² | R¹³ | R¹⁴ |
|---|---|---|---|---|
| 13 | —(CH$_2$)$_2$— | —(CH$_2$)$_2$— | Me | Me |
| 14 | —(CH$_2$)$_3$— | —(CH$_2$)$_3$— | Me | Me |
| 15 | —(CH$_2$)$_3$— | —CH$_2$OCH$_2$CH(OH)— | H | H |

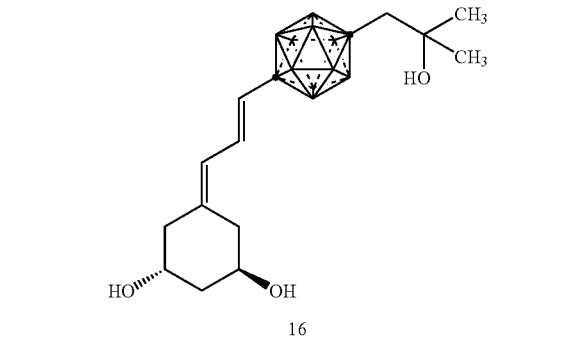

16

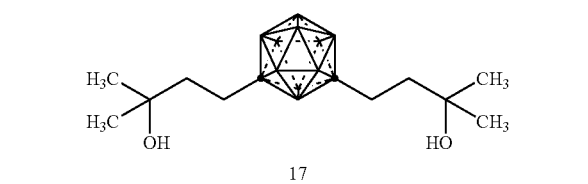

17

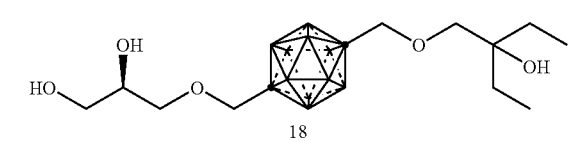

18

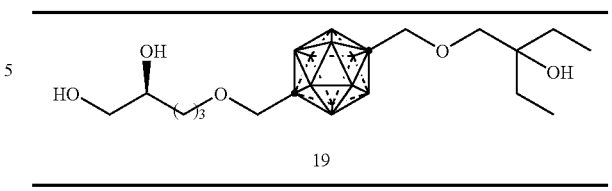

19

The compounds represented by the formula (I) may have one or more asymmetric carbons, and arbitrary optical isomers based on an asymmetric carbon, stereoisomers such as diastereoisomers, arbitrary mixtures of stereoisomers, racemates and the like all fall within the scope of the present invention. Further, the compounds of the formula (I) may exist as acid addition salts or base addition salts depending on types of substituents, and they also fall within the scope of the present invention. Examples of the acid addition salts include, for example, mineral acid salts such as hydrochlorides, sulfates, and nitrates, and organic acid salts such as p-toluenesulfonates and maleates, and examples of the base addition salts include, for example, metal salts such as sodium salts, potassium salts and calcium salts, ammonium salts, organic amine salts such as triethylamine salts and the like. Besides these examples, amino acid salts such as glycine salts, and intramolecular salts (zwitterions) also fall within the scope of the present invention. Furthermore, the compounds and salts thereof according to the present invention may form hydrates or solvates, and all of these substances also fall within the scope of the present invention.

Methods for producing typical compounds falling within the scope of the formula (I) are specifically described in detail in the examples in the specification. Those skilled in the art will be able to produce any of the compounds falling within the scope of the general formula (I) by referring to the specific methods for preparation described in the examples, by suitably choosing starting compounds, reaction conditions, reagents and the like, and by appropriately modifying or altering these methods as required. In addition, methods for producing various compounds having a dicarba-closo-dodecaborane-yl group are described in International Patent Publication WO00/43016, and the disclosure of this publication is incorporated in the specification by reference. Furthermore, methods for producing various compounds having a dicarba-closo-dodecaborane-yl group are also described in other references such as J. Chem. Soc. Dalton Trans., pp. 401–411, 1998; Zh. Obshch. Khim., 41, pp. 1516–20, 1971; J. Chem. Soc. Dalton Trans., pp. 401–411, 1998 and the like, and the disclosures of these literatures are also incorporated in the specification by reference.

The compounds represented by the formula (I) per se have vitamin D-like actions, or they can markedly enhance actions of vitamin D, even where they have substantially no vitamin D-like actions. Therefore, the medicaments comprising the compounds of the present invention represented by the formula (I) as an active ingredient are useful as agents exerting vitamin D actions or agents for enhancing vitamin D actions, and they can be used as, for example, medicaments for prophylactic and/or therapeutic treatment of diseases including rickets, osteomalacia, osteoporosis, bone diseases based on nephropathy, hypoparathyroidism, skin diseases such as psoriasis, cancers (for example, leukemia, breast cancer, and prostatic cancer) and the like.

As the active ingredient of the medicament of the present invention, the compound represented by the aforementioned formula (I) or a physiologically acceptable salt thereof, a hydrate thereof or a solvate thereof can be used. As the medicament of the present invention, the aforementioned active ingredient, per se, may be administered. However, generally it is desirable that a pharmaceutical composition is formulated which comprises the aforementioned active ingredient and one or more pharmaceutical additives and then administered. The route of administration of the medicament of the present invention is not limited. The medicament can be administered orally or parenterally.

Examples of the pharmaceutical compositions suitable for oral administrations include tablets, capsules, powders, subtilized granules, granules, liquids, syrups and the like. Examples of the pharmaceutical compositions suitable for parenteral administrations include injections, drip infusions, suppositories, inhalants, eye drops, nasal drops, transdermally-absorbable formulation, ointments, creams, patches and the like. Examples of pharmaceutical additives include excipients, disintegrators or disintegrating aids, binders, lubricants, coating agents, colorants, diluents, base materials, dissolving agents or solubilizers, isotonic agents, pH modifiers, stabilizers, propellants, adhesives and the like. Appropriate additives can be chosen and used depending on the type of the pharmaceutical composition. The doses of the medicament of the present invention are not particularly limited, and suitable doses can appropriately be chosen depending on the conditions such as the kind of the compound as an active ingredient, a purpose of preventive or therapeutic treatment, the type of a disease, the age and symptoms of a patient, the route of administration and the like.

EXAMPLES

The present invention will be more specifically explained by referring to the following examples. However, the scope of the present invention is not limited to these examples. The compound numbers in the examples correspond to those in the schemes. Further, in the examples, 1,7-dicarba-closo-dodecaborane is referred to as m-carborane, and 1,12-dicarba-closo-dodecaborane is referred to as p-carborane.

Example 1

Synthesis of Compounds 1 and 13

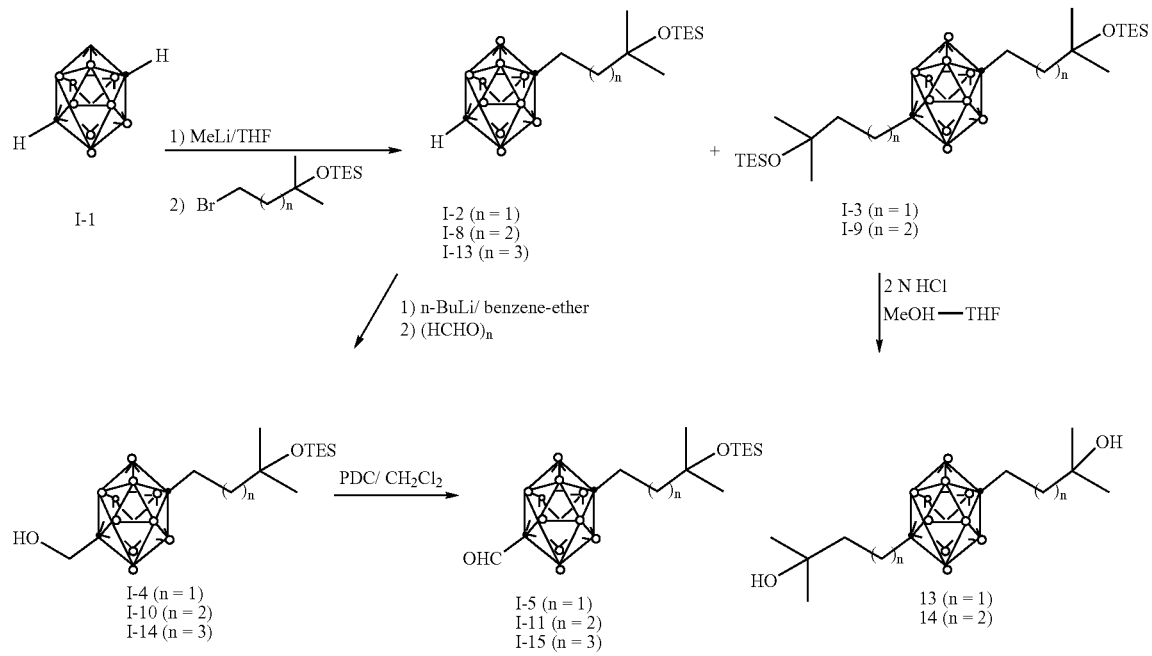

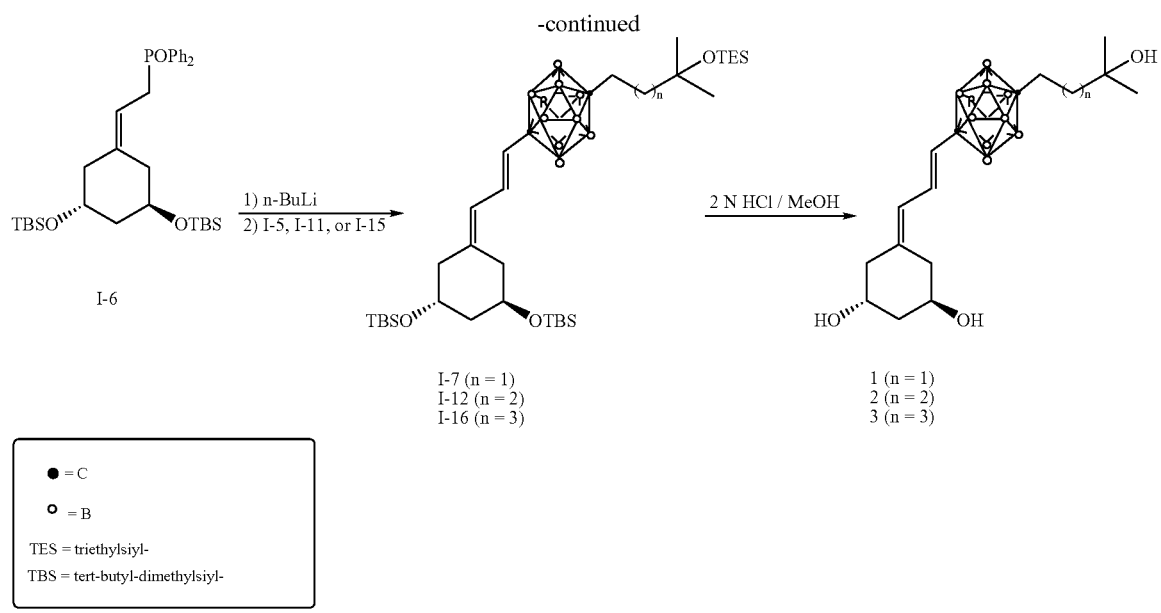

● = C
○ = B
TES = triethylsiyl-
TBS = tert-butyl-dimethylsiyl-

Methyl lithium (1.14 M ether solution, 9.1 ml) was slowly added dropwise to a solution of p-carborane (I-1, 1 g) dissolved in anhydrous tetrahydrofuran (THF, 30 ml) at 0° C. under an argon flow, and then the mixture was stirred at room temperature for 5 hours. The reaction mixture was cooled again to 0° C., and a solution of 1-bromo-3-methyl-3-triethylsilyloxybutane (2.0 g) in THF (5 ml) was slowly added. The reaction mixture was stirred at room temperature for 24 hours, then poured into water and extracted with ethyl acetate. The organic phase was washed with brine and dehydrated over $MgSO_4$. The organic phase was filtered and evaporated, and then the residue was purified by silica gel column chromatography (hexane) to give Compounds I-2 and I-3.

Compound I-2: $^1$H-NMR (CDCl$_3$, 400 MHz) δ: 2.62 (1H, s), 2.76–1.50 (10H, br m), 1.73 (2H, m), 1.24 (2H, m), 1.08 (6H, s), 0.90 (9H, t, J=7.9 Hz), 0.51 (6H, q, J=7.9 Hz)

Compound I-3: $^1$H-NMR (CDCl$_3$, 400 MHz) δ: 1.50–2.80 (10H, br m), 1.72 (4H, m), 1.23 (4H, m), 1.07 (12H, s), 0.90 (18H, t, J=7.9 Hz), 0.51 (12H, q, J=7.9 Hz)

Compound I-2 (300 mg) was dissolved in a mixed solution of anhydrous benzene (2 ml) and anhydrous ether (1 ml), n-BuLi (1.60 M hexane solution, 1.1 ml) was slowly added dropwise to the solution at 0° C. under an argon flow, and then the mixture was stirred at room temperature for 1 hour. The reaction mixture was cooled again to 0° C., paraformaldehyde (55.6 mg and 1.74 mmol) was added, and the mixture was stirred at 0° C. to 10° C. for 5 hours. 2 N HCl was added to the reaction mixture, and the mixture was extracted with ethyl acetate. The organic phase was washed with brine and dehydrated over $MgSO_4$. The organic phase was filtered and evaporated, and the residue was purified by silica gel column chromatography (AcOEt:n-hexane=1:4) to give Compound I-4 (297 mg, 37% from p-carborane).

Compound I-4: $^1$H-NMR (CDCl$_3$, 400 MHz) δ: 3.49 (2H, d, J=7.9 Hz), 2.80–1.50 (10H, br m), 1.75 (2H, m), 1.50 (1H, t, J=7.3 Hz), 1.24 (2H, m), 1.08 (6H, s), 0.91 (9H, t, J=8.0 Hz), 0.51 (6H, q, J=7.9 Hz)

Compound I-4 (297 mg, 0.792 mmol) was added to a suspension of pyridinium dichromate (608 mg, 1.58 mmol) in anhydrous methylene chloride (5 ml) and stirred for 54 hours. The reaction mixture was filtered through Celite and concentrated. The residue was purified by silica gel column chromatography (AcOEt:n-hexane=1:10) to give Compound I-5 (152 mg, 51%).

Compound I-5: $^1$H-NMR (CDCl$_3$, 400 MHz) δ: 8.82 (1H, s), 2.93–1.50 (10H, br m), 1.77 (2H, m), 1.24 (2H, m), 1.09 (6H, s), 0.91 (9H, t, J=7.9 Hz), 0.52 (6H, q, J=7.9 Hz)

Compound I-6 (280 mg, 0.49 mmol) was dissolved in THF (4 ml), n-BuLi (1.60 M hexane solution, 0.29 ml) was slowly added dropwise at −78° C. under an argon flow, and the mixture was stirred for 15 minutes. A solution of Compound I-5 (152 mg, 0.408 mmol) in anhydrous THF (1 ml) was added dropwise to the reaction mixture, and the mixture was stirred at −78° C. for 1 hour and then at room temperature for 5 hours. The reaction mixture was poured into water and extracted with ethyl acetate. The organic phase was washed with brine and dehydrated over $MgSO_4$. The organic phase was filtered and evaporated, and the residue was purified by silica gel column chromatography (AcOEt:n-hexane=1:4) to give Compound I-7 (143 mg, 49%).

Compound I-7: $^1$H-NMR (CDCl3, 400 MHz) δ: 6.20 (1H, dd, J=10.8, 14.8 Hz), 5.63 (1H, d, J=11.4 Hz), 5.29 (1H, d, J=15.0 Hz), 4.09 (1H, m), 3.99 (1H, m), 2.90–1.60 (10H, br m), 2.32 (2H, m), 2.15 (1H, m), 2.03 (1H, m), 1.79 (1H, m), 1.73 (2H, m), 1.60 (1H, m), 1.23 (2H, m), 1.07 (6H, s), 0.91 (9H, t, J=7.9 Hz), 0.86 (9H, s), 0.85 (9H, s), 0.51 (6H, q, J=7.9 Hz), 0.06 (3H, s), 0.05 (3H, s), 0.02 (6H, s)

Compound I-7 (143 mg, 0.198 mmol) was dissolved in a mixed solvent of methanol (4 ml) and THF (3 ml), 2 N hydrochloric acid (1 ml) was added, and the mixture was stirred at room temperature for 30 minutes. The reaction mixture was poured into water and extracted with ethyl acetate. The organic phase was washed with brine and dehydrated over $MgSO_4$. The organic phase was filtered and evaporated, and the residue was purified by silica gel column chromatography (AcOEt:n-hexane=4:1) to give Compound 1 (69 mg, 91%).

Compound 1: colorless prisms (CH$_2$Cl$_2$-n-hexane); mp 154–155° C. $^1$H-NMR (CDCl$_3$, 400 MHz) δ: 6.24 (1H, dd, J=11.1, 14.9 Hz), 5.74 (1H, d, J=11.4 Hz), 5.36 (1H, d, J=14.8 Hz), 4.09 (2H, m), 2.90–1.60 (10H, br m), 2.61 (1H, dd, J=3.5, 13.4 Hz), 2.41 (1H, dd, J=3.5, 13.6 Hz), 2.21 (1H, dd, J=7.6, 13.8 Hz), 2.14 (1H, dd, J=6.7, 13.6 Hz), 1.90 (1H, m), 1.84 (1H, m), 1.74 (2H, m), 1.30 (2H, m), 1.11 (6H, s)

Compound I-3 (369 mg, 0.676 mmol) was dissolved in a mixed solvent of methanol (2 ml) and THF (4 ml), 2 N hydrochloric acid (1 ml) was added, and the mixture was stirred at room temperature for 30 minutes. The reaction mixture was poured into water and extracted with ethyl acetate. The organic phase was washed with brine and dehydrated over MgSO$_4$. The organic phase was filtered and evaporated, and the residue was purified by silica gel column chromatography (AcOEt:n-hexane=1:2) to give Compound 13.(166 mg, 78%).

Compound 13: colorless flakes (CH$_2$Cl$_2$-n-hexane); mp 130–131° C.; Anal. Calcd. for C$_{12}$B$_{10}$H$_{32}$O$_2$: C, 45.54; H, 10.19. Found: C.45.50; H, 9.95. $^1$H-NMR (CDCl$_3$, 400 MHz) δ: 2.80–1.50 (10H, br m), 1.73 (4H, m), 1.29 (4H, m), 1.10 (12H, s), 0.99 (2H, s)

Example 2

Synthesis of Compounds 2 and 14

The compounds were prepared according to the method of Example 1 by using p-carborane (I-1) and 1-bromo-4-methyl-4-triethylsilyloxypentane as the starting materials.

Compound 2: colorless powder (AcOEt-n-hexane); mp 162–163° C.; Anal. calcd. for C$_{17}$B$_{10}$H$_{36}$O$_3$: C, 51.49; H, 9.15. Found: C.51.24; H, 8.95. $^1$H-NMR (CDCl$_3$, 400 MHz) δ: 6.23 (1H, dd, J=11.0, 14.7 Hz), 5.74 (1H, d, J=10.8 Hz), 5.36 (1H, d, J=14.7 Hz), 4.10 (2H, m), 2.90–1.60 (10H, br m), 2.61 (1H, dd, J=3.8, 13.1 Hz), 2.41 (1H, dd, J=3.5, 13.6 Hz), 2.21 (1H, dd, J=7.7, 13.0 Hz), 2.13 (1H, dd, J=6.8, 13.6 Hz), 1.91 (1H, m), 1.82 (1H, m), 1.61 (2H, m), 1.44 (1H, d, J=4.9 Hz), 1.38 (1H, d, J=4.9 Hz), 1.22 (4H, m), 1.16 (6H, s), 1.12 (1H, s)

Compound 14: colorless flocculent substance (CH$_2$Cl$_2$-n-hexane); mp 89–90° C.; Anal. Calcd. for C$_{14}$B$_{10}$H$_{36}$O$_2$: C, 48.80; H, 10.53. Found: C, 49.09; H, 10.29. $^1$H-NMR (CDCl$_3$, 400 MHz) δ: 2.90–1.50 (10H, br m), 1.92 (4H, m), 1.43 (4H, m), 1.35 (4H, m), 1.21 (12H, s), 1.16 (2H, br s)

Example 3

Synthesis of Compound 3

The compound was prepared according to the method of Example 1 by using p-carborane (I-1) and 1-bromo-5-methyl-5-triethylsilyloxyhexane as the starting materials.

Compound 3: $^1$H-NMR (CDCl$_3$, 400 MHz) δ: 6.24 (1H, dd, J=11.1, 14.9 Hz), 5.74 (1H, d, J=11.0 Hz), 5.36 (1H, d, J=14.8 Hz), 4.09 (2H, m), 2.60 (1H, dd, J=3.9, 13.5 Hz), 2.40 (1H, dd, J=3.8, 13.4 Hz), 2.21 (1H, dd, J=7.8, 13.3 Hz), 2.13 (1H, dd, J=6.7, 13.3 Hz), 1.89 (1H, m), 1.81 (1H, m), 1.36 (2H, m), 1.16 (6H, m), 1.16 (6H, s)

Example 4

Synthesis of Compound 4

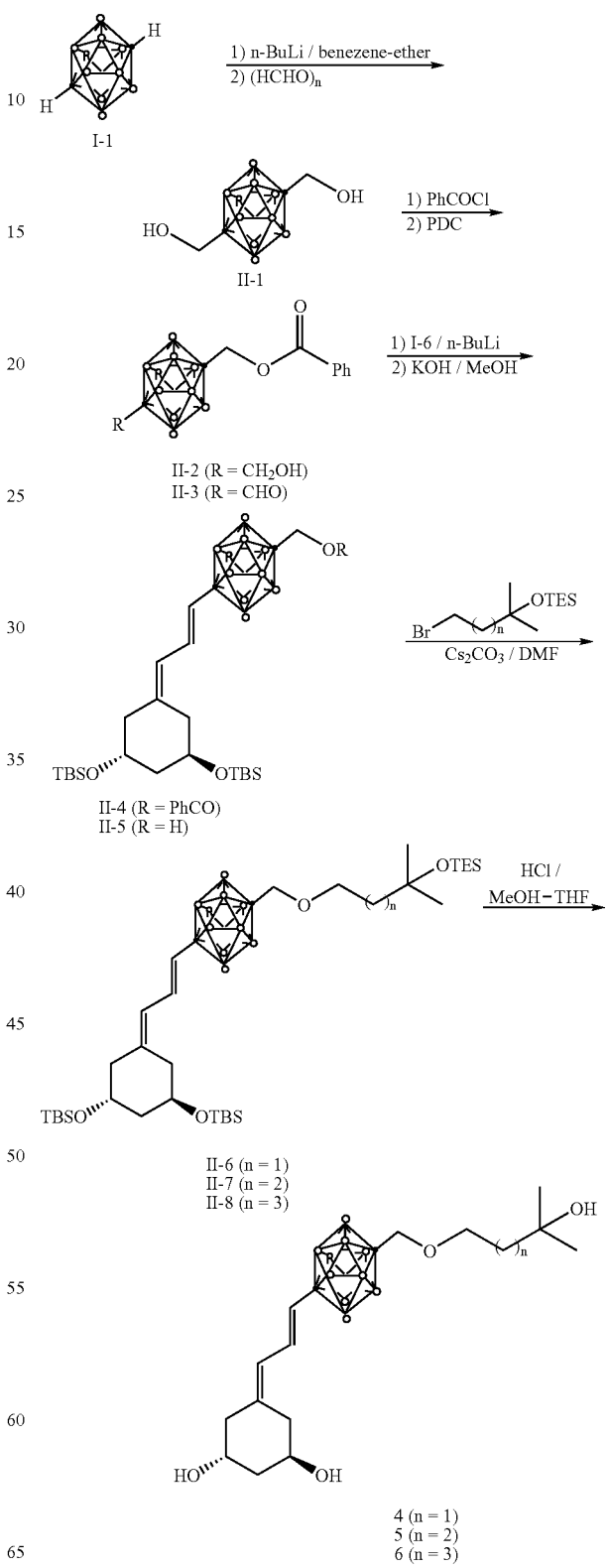

p-Carborane (I-1, 5.0 g) was dissolved in a mixed solution of anhydrous benzene (100 ml) and anhydrous ether (50 ml), n-BuLi (1.60 M hexane solution, 48.6 ml) was slowly added dropwise at 0° C. under an argon flow, and the mixture was stirred at room temperature for 1 hour. The reaction mixture was cooled again to 0° C., paraformaldehyde (2.44 g and 76.4 mmol) was added, and the mixture was stirred at room temperature for 4 hours. 2 N HCl was added to the reaction mixture, and the mixture was extracted with ethyl acetate. The organic phase was washed with brine and dehydrated over $MgSO_4$. The organic phase was filtered and evaporated, and the residue was purified by silica gel column chromatography (AcOEt:n-hexane=1:20) to give Compound II-1 (2.91 g, 41%).

Compound II-1: $^1$H-NMR ($CDCl_3$, 400 MHz) δ: 3.51 (4H, d, J=7.3 Hz), 1.60–2.90 (10H, br s), 1.55 (2H, t, J=7.3 Hz)

Compound II-1 (2.7 g, 13.2 mmol) was dissolved in anhydrous methylene chloride (25 ml) and pyridine (10 ml), benzoic acid chloride (1.52 ml, 13.2 mmol) was added under an argon flow, and the mixture was stirred at room temperature for 15 hours. 2 N HCl was added to the reaction mixture, and the mixture was extracted with methylene chloride. The organic phase was washed with brine and dehydrated over $MgSO_4$. The organic phase was filtered and evaporated, and the residue was purified by silica gel column chromatography (AcOEt:n-hexane=1:5) to give Compound II-2 (2.0 g, 49%).

Compound II-2: $^1$H-NMR ($CDCl_3$, 400 MHz) δ: 7.99 (2H, d, J=8.3 Hz), 7.59 (1H, t, J=7.4 Hz), 7.45 (2H, t, J=7.7 Hz), 4.22 (2H, s), 3.51 (2H, d, J=7.3 Hz), 1.64 (1H, t, J=7.4 Hz)

Compound II-2 (1.0 g, 3.24 mmol) was added to a suspension of pyridinium dichromate (2.49 g, 6.49 mmol) in anhydrous methylene chloride (15 ml) and stirred for 24 hours. The reaction mixture was filtered through Celite and concentrated. The residue was purified by silica gel column chromatography (AcOEt:n-hexane=1:5) to give Compound II-3 (584 mg, 59%).

Compound II-3: $^1$H-NMR ($CDCl_3$, 400 MHz) δ: 8.82. (1H, s), 7.99 (2H, d, J=8.5 Hz), 7.60 (1H, t, J=7.4 Hz), 7.46 (2H, t, J=7.7 Hz), 4.23 (2H, s)

Compound I-6 (1.58 mg, 2.77 mmol) was dissolved in THF (15 ml), n-BuLi (1.60 M hexane solution, 1.74 ml) was slowly added dropwise at –78° C. under an argon flow, and the mixture was stirred for 15 minutes. A solution of Compound II-3 (772 mg, 2.52 mmol) in anhydrous THF (10 ml) was added dropwise to the reaction mixture. The mixture was stirred at –78° C. for 4 hours and then at room temperature for 1 hour. The reaction mixture was poured into water and extracted with ethyl acetate. The organic phase was washed with brine and dehydrated over $MgSO_4$. The organic phase was filtered and evaporated, and the residue was purified by silica gel column chromatography (CH2Cl2:n-hexane=1:10->AcOEt:n-hexane=1:50->AcOEt:n-hexane=1:10) to give Compound II-4 (383 mg, 23%).

Compound II-4: $^1$H-NMR ($CDCl_3$, 400 MHz) δ: 8.00 (2H, d, J=8.4 Hz), 7.58 (1H, t, J=7.4 Hz), 7.45 (2H, t, J=7.6 Hz), 6.21 (1H, dd, J=11.0, 15.0 Hz), 5.64 (1H, d, J=10.8 Hz), 5.30 (1H, d, J=15.0 Hz), 4.21 (2H, s), 4.10 (1H, m), 3.99 (1H, m), 2.32 (2H, m), 2.15 (1H, d, J=10.8 Hz), 2.04 (1H, dd, J=8.8, 13.2 Hz), 1.78 (1H, m), 1.62 (1H, m), 0.86 (9H, s), 0.85 (9H, s), 0.06 (3H, s), 0.05 (3H, s), 0.02 (6H, s)

Compound II-4 (383 mg, 0.581 mmol) was dissolved in a mixed solvent of methanol (6 ml) and THF (4 ml), 1 N potassium hydroxide (2 ml) was added, and the mixture was stirred at room temperature for 1 hour. The reaction mixture was poured into water and extracted with ethyl acetate. The organic phase was washed with brine and dehydrated over $MgSO_4$. The organic phase was washed with brine and dehydrated over $MgSO_4$. The organic phase was filtered and evaporated, and the residue was purified by silica gel column chromatography (AcOEt:n-hexane=1:10) to give Compound II-5 (275 mg, 85%).

Compound II-5: $^1$H-NMR ($CDCl_3$, 400 MHz) δ: 6.21 (1H, dd, J=11.1, 14.9 Hz), 5.64 (1H, d, J=10.8 Hz), 5.30 (1H, d, J=14.7 Hz), 4.10 (1H, m), 3.99 (1H, m), 3.50 (2H, d, J=7.5 Hz), 2.32 (2H, m), 2.16 (1H, m), 2.04 (1H, dd, J=8.7, 12.2 Hz), 1.80 (1H, m), 1.62 (1H, m), 0.86 (9H, s), 0.85 (9H, s), 0.06 (3H, s), 0.05 (3H, s), 0.02 (6H, s)

Compound II-5 (59 mg, 0.106 mmol), cesium carbonate (173 mg, 0.530 mmol) and 1-bromo-3-methyl-3-triethylsilyloxybutane (54 mg, 0.192 mmol) were dissolved in anhydrous dimethylformamide (DMF, 2 ml) and heated at 80° C. for 24 hours under an argon flow. Cesium carbonate (173 mg, 0.530 mmol) was further added, and the mixture was heated for 30 hours. The reaction mixture was cooled, poured into water and extracted with ethyl acetate. The organic phase was washed with brine and dehydrated over $MgSO_4$. The organic phase was filtered and evaporated, and the residue was purified by silica gel column chromatography (AcOEt:n-hexane=1:40->1:10) to give Compound II-6 (13 mg, 17%) and the starting material, Compound II-5 (25 mg, 42%).

Compound II-6: $^1$H-NMR ($CDCl_3$, 400 MHz) δ: 6.19 (1H, dd, J=11.0, 14.8 Hz), 5.63 (1H, d, J=11.2 Hz), 5.29 (1H, d, J=14.8 Hz), 4.09 (1H, m), 3.99 (1H, m), 3.41 (2H, t, J=7.0 Hz), 3.27 (2H, s), 2.32 (2H, m), 2.15 (1H, d, J=13.0 Hz), 2.04 (1H, m), 1.78 (1H, m), 1.63 (2H, t, J=7.0 Hz), 1.62 (1H, m), 1.19 (6H, s)

Compound II-6 was dissolved in a mixed solvent of methanol (1 ml) and THF (1 ml), 2 N hydrochloric acid (0.5 ml) was added, and the mixture was stirred at room temperature for 30 minutes. The reaction mixture was poured into water and extracted with ethyl acetate. The organic phase was washed with brine and dehydrated over $MgSO_4$. The organic phase was filtered and evaporated, and the residue was purified by silica gel column chromatography (AcOEt:n-hexane=1:1->4:1->5:1) to give Compound 4 (7.8 mg, 61%).

Compound 4: HRMS Calcd. for $C_{17}H_{36}O_4{}^{10}B_2{}^{11}B_8$, 412.3617. Found 412.3623 (+0.7 mmu). $^1$H-NMR ($CDCl_3$, 400 MHz) δ: 6.22 (1H, dd, J=11.1, 14.9 Hz), 5.73 (1H, d, J=11.0 Hz), 5.35 (1H, d, J=14.8 Hz), 4.09 (2H, m), 3.52 (2H, t, J=5.9 Hz), 3.31 (2H, s), 2.60 (1H, dd, J=3.5, 13.4 Hz), 2.40 (1H, dd, J=3.5, 13.4 Hz), 2.21 (1H, dd, J=7.9, 13.4 Hz), 2.13 (1H, dd, J=6.5, 13.3 Hz), 1.90 (1H, m), 1.82 (1H, ddd, J=3.8, 7.8, 13.3 Hz), 1.70 (2H, t, J=5.9 Hz), 1.21 (6H, s)

Example 5

Synthesis of Compound 5

The compound was prepared from Compound II-5 and 1-bromo-4-methyl-4-triethylsilyloxypentane according to the method of Example 4.

Compound 5: HRMS Calcd. for $C_{18}H_{38}O_4{}^{10}B_2{}^{11}B_8$, 426.3773. Found 426.3753 (–2.0 mmu). $^1$H-NMR ($CDCl_3$, 400 MHz) δ: 6.23 (1H, dd, J=11.1, 14.9 Hz), 5.73 (1H, d, J=10.8 Hz), 5.36 (1H, d, J=15.0 Hz), 4.09 (2H, m), 3.32 (2H, t, J=6.1 Hz), 3.30 (2H, s), 2.60 (1H, dd, J=3.8, 13.4 Hz), 2.40 (1H, dd, J=3.8, 13.5 Hz), 2.21 (1H, dd, J=7.7, 13.4 Hz), 2.13 (1H, dd, J=6.6, 13.6 Hz), 1.90 (1H, m), 1.82 (1H, ddd, J=3.3, 7.9, 13.4 Hz), 1.60 (2H, m), 1.26 (2H, m), 1.21 (6H, s)

Example 6

Synthesis of Compound 6

The compound was prepared from Compound II-5 and 1-bromo-5-methyl-5-triethylsilyloxyhexane according to the method of Example 4.

Compound 6: HRMS Calcd. for $C_{19}H_{40}O_4{}^{10}B_2{}^{11}B_8$, 440.3930. Found 440.3948 (+1.8 mmu). $^1$H-NMR (CDCl$_3$, 400 MHz) δ: 6.23 (1H, dd, J=11.1, 14.9 Hz), 5.73 (1H, d, J=11.0 Hz), 5.36 (1H, d, J=14.8 Hz), 4.08 (2H, m), 3.30 (2H, t, J=6.3 Hz), 3.29 (2H, s), 2.60 (1H, dd, J=3.8, 13.6 Hz), 2.40 (1H, dd, J=3.8, 13.5 Hz), 2.21 (1H, dd, J=7.7, 13.2 Hz), 2.13 (1H, dd, J=6.6, 13.4 Hz), 1.90 (1H, m), 1.81 (1H, ddd, J=3.3, 7.9, 12.7 Hz), 1.51–1.33 (6H, m), 1.21 (6H, s)

Example 7

Synthesis of Compounds 7 and 9

Compound III-1: $^1$H-NMR (CDCl$_3$, 400 MHz) δ: 6.20 (1H, dd, J=11.0, 15.0 Hz), 5.63 (1H, d, J=11.0 Hz), 5.30 (1H, d, J=14.8 Hz), 4.09 (1H, m), 3.99 (1H, m), 3.89 (2H, s), 3.38 (2H, s), 2.32 (2H, m), 2.15 (1H, d, J=11.2 Hz), 2.03 (1H, dd, J=8.5, 12.5 Hz), 1.80 (1H, m), 1.62 (1H, m), 0.86 (9H, s), 0.85 (9H, s), 0.06 (3H, s), 0.05 (3H, s), 0.02 (6H, s)

Compound III-1 was dissolved in a mixed solvent of methanol (1 ml) and THF (0.5 ml), 2 N hydrochloric acid (0.5 ml) was added, and the mixture was stirred at room temperature for 30 minutes. The reaction mixture was poured into water and extracted with ethyl acetate. The organic phase was washed with brine and dehydrated over MgSO$_4$. The organic phase was filtered and evaporated, and the residue was purified by silica gel column chromatography (AcOEt:n-hexane=1:1->4:1) to give Compound III-2 (14 mg, 92%).

Compound III-2: $^1$H-NMR (CDCl$_3$, 400 MHz) δ: 6.24 (1H, dd, J=11.1, 14.9 Hz), 5.74 (1H, d, J=10.8 Hz), 5.36 (1H, d, J=14.8 Hz), 4.09 (2H, m), 3.89 (2H, s), 3.38 (2H, s), 2.61

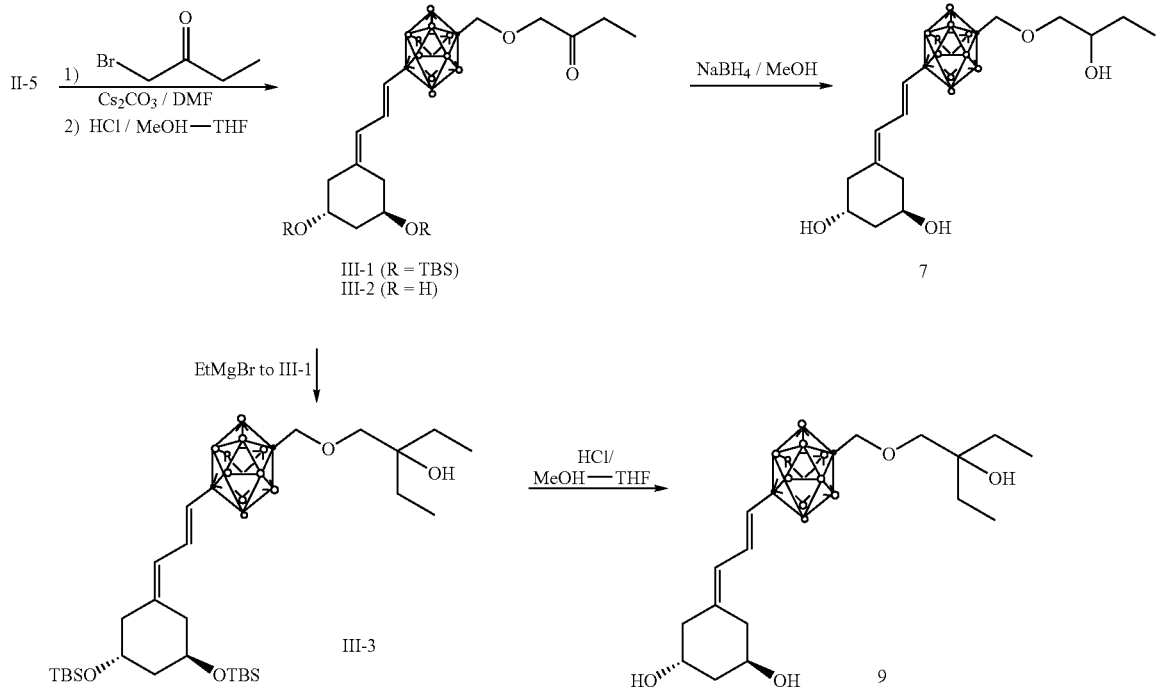

Compound II-5 (55 mg, 0.099 mmol), cesium carbonate (161 mg, 0.500 mmol) and 1-bromo-2-butanone (0.02 ml, 0.176 mmol) were dissolved in anhydrous DMF (2 ml) and stirred at room temperature for 5 hours under an argon flow. Cesium carbonate (161 mg, 0.500 mmol) and 1-bromo-2-butanone (0.02 ml, 0.176 mmol) were further added, and the mixture was stirred for 19 hours and for 6 hours at 50° C. The reaction mixture was cooled, poured into water and extracted with ethyl acetate. The organic phase was washed with brine and dehydrated over MgSO$_4$. The organic phase was filtered and evaporated, and the residue was purified by silica gel column chromatography (AcOEt:n-hexane=1:20->1:10) to give Compound III-1 (24 mg, 38%) and the starting material, Compound II-5 (22 mg, 39%).

(1H, dd, J=3.8, 13.3 Hz), 2.45 (2H, q, J=7.3 Hz), 2.41 (1H, dd, J=3.7, 13.6 Hz), 2.21 (1H, dd, J=7.6, 13.3 Hz), 2.13 (1H, dd, J=6.5, 13.5 Hz), 1.91 (1H, m), 1.82 (1H, ddd, J=3.7, 7.9, 13.5 Hz), 1.04 (3H, t, J=7.3 Hz)

Compound III-2 (14 mg, 0.035 mmol) was dissolved in methanol (1 ml), NaBH$_4$ (2.6 mg, 0.069 mmol) was added at 0° C., and the mixture was stirred for 1 hour. The reaction mixture was poured into water and extracted with ethyl acetate. The organic phase was washed with brine and dehydrated over MgSO$_4$. The organic phase was filtered and evaporated, and the residue was purified by silica gel column chromatography (AcOEt:n-hexane=4:1) to give Compound 7 (7.9 mg, 57%).

Compound 7: HRMS Calcd. for $C_{16}H_{34}O_4{}^{10}B_2{}^{11}B_8$, 398.3460. Found 398.3445 (−1.5 mmu). $^1$H-NMR (CDCl$_3$, 400 MHz) δ: 6.23 (1H, dd, J=11.0, 14.8 Hz), 5.75 (1H, d, J=11.4 Hz), 5.36 (1H, d, J=14.8 Hz), 4.09 (2H, m), 3.61 (1H, m), 3.37 (1H, d, J=10.8 Hz), 3.34 (1H, dd, J=3.0, 9.3 Hz), 3.33 (1H, d, J=10.6 Hz), 3.16 (1H, dd, J=7.5, 9.3 Hz), 2.59 (1H, dd, J=3.8, 13.4 Hz), 2.40 (1H, dd, J=3.7, 13.4 Hz), 2.21 (1H, dd, J=7.7, 13.4 Hz), 2.13 (1H, dd, J=6.5, 13.5 Hz), 1.90 (1H, m), 1.81 (1H, ddd, J=3.7, 7.9, 13.0 Hz), 1.43 (2H, m), 0.93 (3H, t, J=7.5 Hz)

Compound III-1 (20 mg, 0.031 mmol) was dissolved in THF (1 ml), and EtMgBr (1.0 M THF solution, 0.04 ml) was added dropwise at 0° C. under an argon flow. The reaction mixture was stirred at room temperature for 21 hours, then saturated aqueous ammonium chloride was added, and the mixture was extracted with ethyl acetate. The organic phase was washed with brine and dehydrated over MgSO$_4$. The organic phase was filtered and evaporated, and the residue was purified by silica gel column chromatography (AcOEt:n-hexane=1:10) to give Compound III-3 (21 mg, quant).

Compound III-3: $^1$H-NMR (CDCl$_3$, 400 MHz) δ: 6.20 (1H, dd, J=11.0, 15.0 Hz), 5.63 (1H, d, J=11.2 Hz), 5.29 (1H, d, J=14.8 Hz), 4.09 (1H, m), 3.99 (1H, m), 3.32 (2H, s), 3.15 (2H, s), 2.32 (2H, m), 2.15 (1H, d, J=10.6 Hz), 2.03 (1H, dd, J=8.3, 12.7 Hz), 1.79 (1H, m), 1.60 (1H, m), 1.48 (2H, dq, J=7.4, 14.0 Hz), 1.43 (2H, dq, J=7.2, 14.4 Hz), 0.86 (9H, s), 0.85 (9H, s), 0.83 (6H, t, J=7.5 Hz), 0.06 (3H, s), 0.05 (3H, s), 0.02 (6H, s)

Compound III-3 (21 mg, 0.032 mmol) was dissolved in a mixed solvent of methanol (1 ml) and THF (0.51 ml), 2 N hydrochloric acid (0.5 ml) was added, and the mixture was stirred at room temperature for 30 minutes. The reaction mixture was poured into water and extracted with ethyl acetate. The organic phase was washed with brine and dehydrated over MgSO$_4$. The organic phase was filtered and evaporated, and the residue was purified by silica gel column chromatography (AcOEt:n-hexane=4:1) to give Compound 9 (11 mg, 77%).

Compound 9: HRMS Calcd. for $C_{18}H_{38}O_4{}^{10}B_2{}^{11}B_8$ 426.3773. Found 426.3787 (+1.4 mmu). $^1$H-NMR (CDCl$_3$, 400 MHz) δ: 6.24 (1H, dd, J=11.1, 14.9 Hz), 5.74 (1H, d, J=10.8 Hz), 5.36 (1H, d, J=14.8 Hz), 4.09 (2H, m), 3.33 (2H, s), 3.15 (2H, s), 2.60 (1H, dd, J=3.5, 13.2 Hz), 2.40 (1H, dd, J=3.5, 13.6 Hz), 2.21 (1H, dd, J=7.8, 13.3 Hz), 2.13 (1H, dd, J=6.6, 13.6 Hz), 1.91 (1H, m), 1.81 (1H, ddd, J=3.6, 8.0, 12.9 Hz), 1.48 (2H, dq, J=7.5, 14.0 Hz), 1.44 (2H, dq, J=7.5, 14.0 Hz), 0.83 (6H, t, J=7.5 Hz)

Example 8

Synthesis of Compound 8

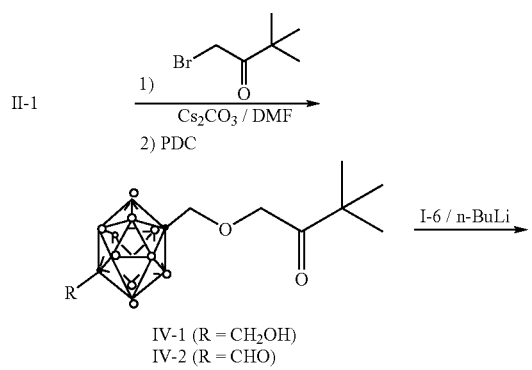

IV-1 (R = CH$_2$OH)
IV-2 (R = CHO)

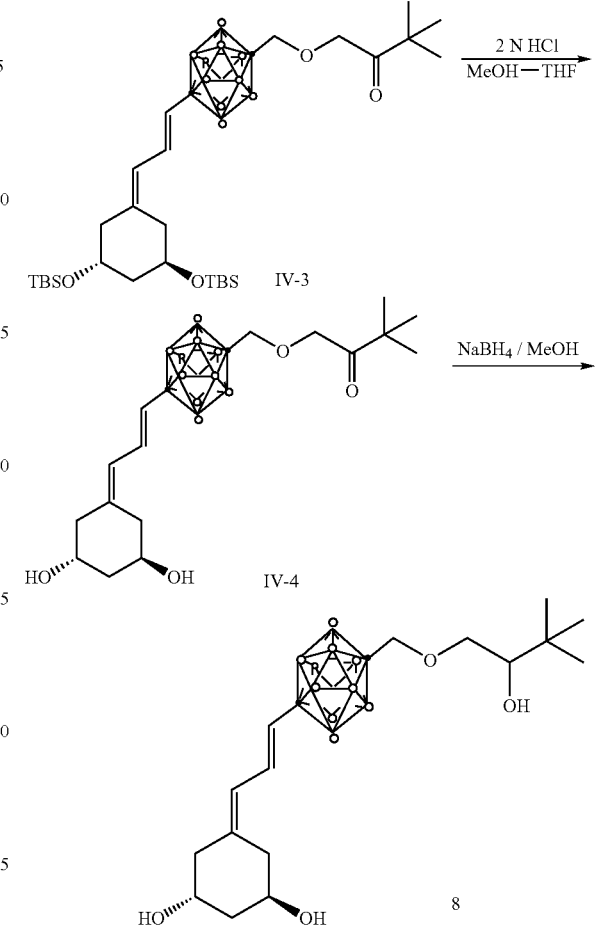

Compound II-1 (1.05 g, 5.12 mmol), cesium carbonate (8.34 g, 25.6 mmol) and 1-chloropinacolin (0.70 ml, 5.14 mmol) were dissolved in anhydrous DMF (100 ml), and the solution was heated at 60° C. for 24 hours under an argon flow. The reaction mixture was cooled, poured into water and extracted with ethyl acetate. The organic phase was washed with brine and dehydrated over MgSO$_4$. The organic phase was filtered and evaporated, and the residue was purified by silica gel column chromatography (AcOEt:n-hexane=1:4) to give Compound IV-1 (423 mg, 278%) and the starting material, Compound II-1 (322 mg, 31%).

Compound IV-1: $^1$H-NMR (CDCl$_3$, 400 MHz) δ: 4.21 (2H, s), 3.49 (2H, d, J=7.3 Hz), 3.40 (2H, s), 1.55 (1H, t, J=7.4 Hz), 1.12 (9H, s)

Compound IV-1 (200 mg, 0.661 mmol) was added to a suspension of pyridinium dichromate (381 mg, 0.992 mmol) in anhydrous methylene chloride (5 ml) and stirred for 54 hours. The reaction mixture was filtered through Celite and concentrated. The residue was purified by silica gel column chromatography (AcOEt:n-hexane=1:6) to give Compound IV-2 (127 mg, 64%).

Compound IV-2: $^1$H-NMR (CDCl$_3$, 400 MHz) δ: 8.81 (1H, s), 4.22 (2H, s), 3.40 (2H, s), 1.12 (9H, s)

Compound I-6 (266 mg, 0.466 mmol) was dissolved in THF (4 ml), n-BuLi (1.60 M hexane solution, 0.29 ml) was slowly added dropwise at −78° C. under an argon flow, and the mixture was stirred for 15 minutes. A solution of Compound IV-2 (127 mg, 0.424 mmol) in anhydrous THF (1 ml) was added dropwise to the reaction mixture. The mixture was stirred at −78° C. for 1 hour and then at room temperature for 5 hours. The reaction mixture was poured into water and extracted with ethyl acetate. The organic phase was washed with brine and dehydrated over MgSO$_4$. The organic phase was filtered and evaporated, and the residue was purified by silica gel column chromatography (AcOEt:n-hexane=1:20) to give Compound IV-3. This crude product was dissolved in a mixed solvent of methanol (2 ml) and THF (1.5 ml), 2 N hydrochloric acid (1 ml) was added, and the mixture was stirred at room temperature for 30 minutes. The reaction mixture was poured into water and extracted with ethyl acetate. The organic phase was washed with brine and dehydrated over MgSO$_4$. The organic phase was filtered and evaporated, and the residue was purified by silica gel column chromatography (AcOEt:n-hexane=1:1->4:1) to give Compound IV-4 (30 mg, 17% from IV-2).

Compound IV-4: $^1$H-NMR (CDCl$_3$, 400 MHz) δ: 6.23 (1H, dd, J=11.0, 14.8 Hz), 5.73 (1H, d, J=11.0 Hz), 5.35 (1H, d, J=14.8 H), 4.21 (2H, s), 4.09 (2H, m), 3.39 (2H, s), 2.60 (1H, dd, J=3.9, 13.5 Hz), 2.40 (1H, dd, J=3.7, 13.6 Hz), 2.21 (1H, dd, J=8.0, 13.5 Hz), 2.13 (1H, dd, J=6.4, 13.6 Hz), 1.90 (1H, m), 1.81 (1H, m), 1.11 (9H, s)

Compound IV-4 (30 mg, 0.070 mmol) was dissolved in methanol (2 ml), NaBH$_4$ was added at 0° C., and the mixture was stirred for 1 hour. The reaction mixture was poured into water and extracted with ethyl acetate. The organic phase was washed with brine and dehydrated over MgSO$_4$. The organic phase was filtered and evaporated to give Compound 8 (31 mg, quant).

Compound 8: HRMS Calcd. for $C_{18}H_{38}O_4{}^{10}B_2{}^{11}B_8$, 426.3773. Found 426.3809 (+3.6 mmu). $^1$H-NMR (CDCl$_3$, 400 MHz) δ: 6.24 (1H, dd, J=11.0, 14.8 Hz), 5.73 (1H, d, J=10.8 Hz), 5.35 (1H, d, J=15.0 Hz), 4.09 (2H, m), 3.44 (1H, dd, J=2.7, 9.0 Hz), 3.37 (1H, dd, J=2.7, 8.8 Hz), 3.37 (1H, d, J=11.2 Hz), 3.33 (1H, d, J=10.8 Hz), 3.19 (1H, t, J=8.9 Hz), 2.60 (1H, dd, J=3.8, 13.5 Hz), 2.40 (1H, dd, J=3.5, 13.6 Hz), 2.21 (1H, dd, J=7.9, 13.4 Hz), 2.13 (1H, dd, J=6.5, 13.5 Hz), 1.90 (1H, m), 1.81 (1H, m), 0.88 (9H, s)

Example 9

Synthesis of Compound 10

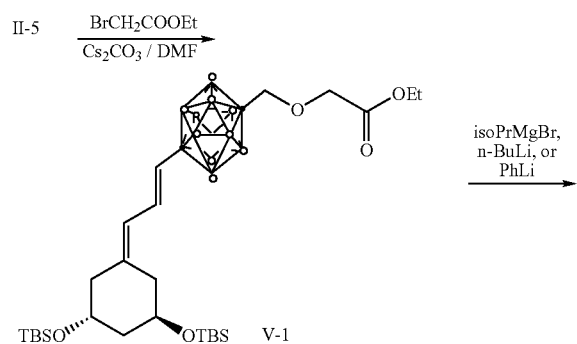

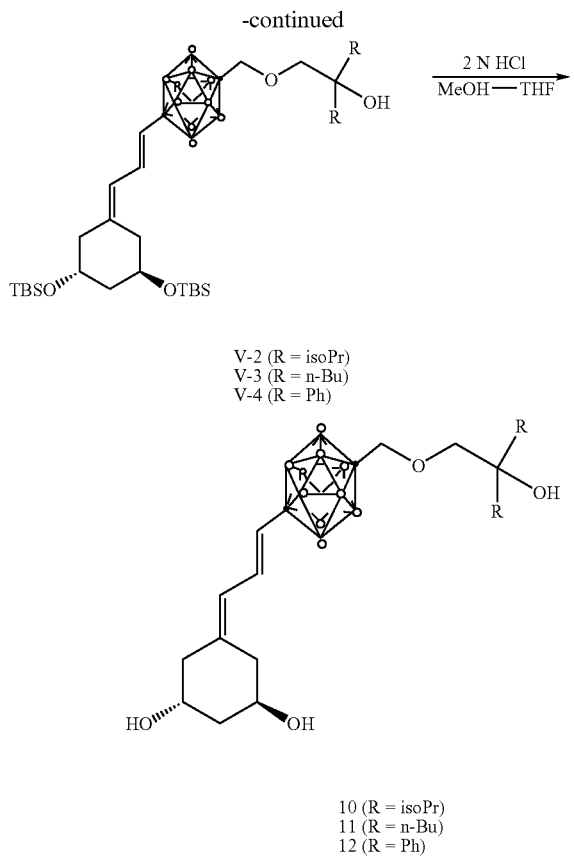

Compound II-5 (114.5 mg, 0.206 mmol), cesium carbonate (336 mg, 1.03 mmol) and ethyl bromoacetate (0.03 ml, 0.258 mmol) were dissolved in anhydrous DMF (3 ml) and heated at 80° C. for 22 hours under an argon flow. Cesium carbonate (336 mg, 1.03 mmol) and ethyl bromoacetate (0.03 ml, 0.258 mmol) were further added, and the mixture was heated for 24 hours. The reaction mixture was cooled, poured into water and extracted with ethyl acetate. The organic phase was washed with brine and dehydrated over MgSO$_4$. The organic phase was filtered and evaporated, and the residue was purified by silica gel column chromatography (AcOEt:n-hexane=1:10) to give Compound V-1 (51 mg, 38%) and the starting material, Compound II-5 (14 mg, 12%).

Compound V-1: $^1$H-NMR (CDCl$_3$, 400 MHz) δ: 6.20 (1H, dd, J=10.8, 15.0 Hz), 5.63 (1H, d, J=11.0 Hz), 5.29 (1H, d, J=15.0 Hz), 4.17 (2H, q, J=7.2 Hz), 4.09 (1H, m), 3.99 (1H, m), 3.96 (2H, s), 3.46 (2H, s), 2.32 (2H, m), 2.15 (1H, d, J=13.2 Hz), 2.03 (1H, dd, J=9.0, 13.2 Hz), 1.80 (1H, m), 1.61 (1H, m), 1.26 (3H, t, J=7.1 Hz), 0.86 (9H, s), 0.85 (9H, s), 0.06 (3H, s), 0.05 (3H, s), 0.02 (6H, s)

Compound V-1 (28 mg, 0.043 mmol) was dissolved in anhydrous THF (1 ml), and i-PrMgBr (0.75 M THF solution, 0.13 ml) was added at 0° C. under an argon flow. After 24 hours, saturated aqueous ammonium chloride was added to the reaction mixture, and the mixture was extracted with ethyl acetate. The organic phase was washed with brine and dehydrated over MgSO$_4$. The organic phase was filtered and evaporated, and the residue was purified by silica gel column chromatography (AcOEt:n-hexane=1:20) to give Compound V-2 (4.5 mg, 15%).

Compound V-2: $^1$H-NMR (CDCl$_3$, 400 MHz) δ: 6.19 (1H, dd, J=11.0, 15.0 Hz), 5.63 (1H, d, J=10.8 Hz), 5.29 (1H, d, J=14.8 Hz), 4.09 (1H, m), 3.99 (1H, m), 3.26 (2H, s), 3.20 (2H, s), 2.32 (2H, m), 2.14 (1H, d, J=14.7 Hz), 2.03 (1H, dd, J=8.5, 13.1 Hz), 1.92 (2H, m), 1.79 (1H, m), 1.61 (1H, m), 0.91 (6H, d, J=7.0 Hz), 0.87 (6H, d, J=7.0 Hz), 0.86 (9H, s), 0.85 (9H, s), 0.06 (3H, s), 0.05 (3H, s), 0.02 (6H, s)

Compound V-2 (4.5 mg, 0.007 mmol) was dissolved in a mixed solvent of methanol (1 ml) and THF (0.5 ml), 2 N hydrochloric acid (0.5 ml) was added, and the mixture was stirred at room temperature for 30 minutes. The reaction mixture was poured into water and extracted with ethyl acetate. The organic phase was washed with brine and dehydrated over MgSO$_4$. The organic phase was filtered and evaporated, and the residue was purified by silica gel column chromatography (AcOEt:n-hexane=4:1) to give Compound 10 (4 mg, quant).

Compound 10: HRMS Calcd. for C$_{20}$H$_{42}$O$_4$$^{10}$B$_2$$^{11}$B$_8$, 454.4086. Found 454.4056 (−3.0 mmu). $^1$H-NMR (CDCl$_3$, 400 MHz) δ: 6.23 (1H, dd, J=11.0, 14.8 Hz), 5.73 (1H, d, J=11.0 Hz), 5.36 (1H, d, J=15.0 Hz), 4.10 (2H, m), 3.65 (1H, s), 3.26 (2H, s), 3.20 (2H, s), 2.61 (1H, dd, J=3.9, 13.5 Hz), 2.40 (1H, dd, J=3.8, 13.7 Hz), 2.21 (1H, dd, J=7.5, 13.2 Hz), 2.11 (1H, m), 1.92 (1H, m), 1.91 (2H, m), 1.81 (1H, ddd, J=3.6, 8.1 13.3 Hz), 0.91 (6H, d, J=6.8 Hz), 0.87 (6H, d, J=7.0 Hz)

Example 10

Synthesis of Compound 11

The compound was prepared from Compound V-1 and n-BuLi according to the method of Example 9.

Compound 11: HRMS Calcd. for C$_{22}$H$_{46}$O$_4$$^{10}$B$_2$$^{11}$B$_8$, 482.4399. Found 482.4392 (−0.8 mmu). $^1$H-NMR (CDCl$_3$, 400 MHz) δ: 6.23 (1H, dd, J=11.0, 15.0 Hz), 5.73 (1H, d, J=11.0 Hz), 5.36 (1H, d, J=15.0 Hz), 4.10 (2H, m), 3.32 (2H, s), 3.14 (2H, s), 2.61 (1H, dd, J=3.8, 13.4 Hz), 2.40 (1H, dd, J=3.3, 13.2 Hz), 2.21 (1H, dd, J=7.7, 13.2 Hz), 2.13 (1H, dd, J=6.6, 13.9 Hz), 1.91 (1H, m), 1.82 (1H, ddd, J=3.4, 8.0 13.3 Hz), 1.41 (4H, m), 1.25 (8H, m), 0.91 (6H, t, J=7.1 Hz)

Example 11

Synthesis of Compound 12

The compound was prepared from Compound V-1 and PhLi according to the method of Example 9.

Compound 12: HRMS Calcd. for C$_{26}$H$_{38}$O$_4$$^{10}$B$_2$$^{11}$B$_8$, 522.3773. Found 522.3788 (−3.5 mmu). $^1$H-NMR (CDCl$_3$, 400 MHz) δ: 7.35–7.22 (10H, m), 6.21 (1H, dd, J=11.0, 15.0 Hz), 5.73 (1H, d, J=10.6 Hz), 5.34 (1H, d, J=15.0 Hz), 4.10 (2H, m), 3.84 (2H, s), 3.41 (2H, s), 3.17 (1H, s), 2.59 (1H, dd, J=3.9, 13.5 Hz), 2.40 (1H, dd, J=3.7, 13.4 Hz), 2.20 (1H, dd, J=8.2, 13.1 Hz), 2.13 (1H, dd, J=6.4, 13.6 Hz), 1.90 (1H, m), 1.80 (1H, ddd, J=3.4, 7.6, 13.6 Hz)

Example 12

Synthesis of Compound 15

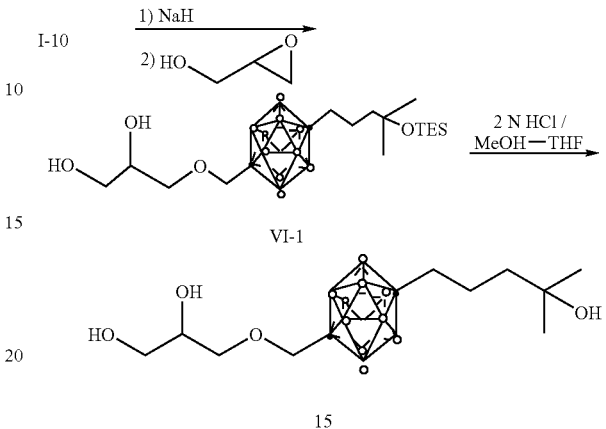

NaH (12 mg, 0.310 mmol) was suspended in anhydrous DMF (2 ml), Compound I-10.(100 mg, 0.257 mmol) was added at 0° C. under an argon flow, and the mixture was stirred at room temperature for 20 hours. Glycidol (0.02 ml, 0.301 mmol) was added to the reaction mixture, and the mixture was heated at 70° C. for 20 hours. The reaction mixture was poured into water and extracted with ethyl acetate. The organic phase was washed with brine and dehydrated over MgSO$_4$. The organic phase was filtered and evaporated, and the residue was purified by silica gel column chromatography (AcOEt:n-hexane=1:2->1:1) to give Compound VI-1 (56 mg, 47%).

Compound VI-1: $^1$H-NMR (CDCl$_3$, 400 MHz) δ: 3.77 (1H, m), 3.68 (1H, ddd, J=4.0, 7.1, 11.4 Hz), 3.61 (1H, dt, J=5.3, 11.4 Hz), 3.42 (2H, m), 3.36 (1H, d, J=10.8 Hz), 3.34 (1H, d, J=10.7 Hz), 2.90–1.60 (10H, br m), 2.41 (1H, d, J=5.5 Hz), 1.93 (1H, br t, J=6.1 Hz), 1.58 (2H, m), 1.5–1.2 (4H, m), 1.13 (6H, s), 0.93 (9H, t, J=7.9 Hz), 0.53 (6H, q, J=7.9 Hz)

Compound VI-1 (56 mg, 0.120 mmol) was dissolved in methanol (4 ml), 2 N hydrochloric acid (1 ml) was added, and the mixture was stirred at room temperature for 30 minutes. The reaction mixture was poured into water and extracted with ethyl acetate. The organic phase was washed with brine and dehydrated over MgSO$_4$. The organic phase was filtered and evaporated, and the residue was purified by silica gel column chromatography (AcOEt:n-hexane=2:1) to give Compound 15 (37 mg, 88%).

Compound 15: colorless leaflets (AcOEt-n-hexane); mp 83–84° C.; Anal. Calcd. for C$_{12}$B$_{10}$H$_{32}$O$_4$: C, 41.36; H, 9.26. Found: C, 41.27; H, 8.99. $^1$H-NMR (CDCl$_3$, 400 MHz) δ: 3.77 (1H, m), 3.68 (1H, ddd, J=4.0, 7.1, 11.4 Hz), 3.61 (1H, dt, J=5.3, 11.4 Hz), 3.42 (2H, m), 3.37 (1H, d, J=10.6 Hz), 3.34 (1H, d, J=10.6 Hz), 2.90–1.60 (10H, br m), 2.41 (1H, d, J=5.5 Hz), 1.92 (1H, dd, J=5.3, 7.0 Hz), 1.62 (2H, m), 1.24 (4H, m), 1.16 (6H, s), 1.11 (1H, s)

Example 13

Synthesis of Compounds 16 and 17

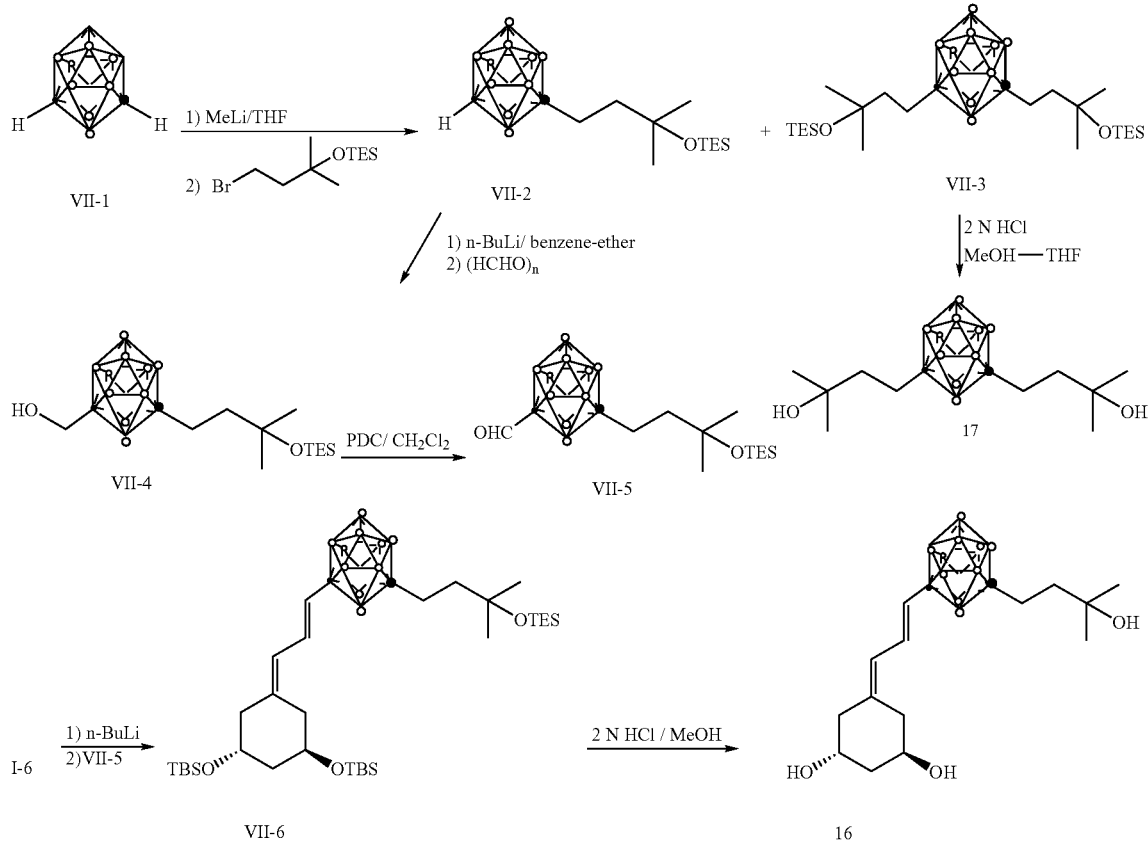

Methyl lithium (1.14 M ether solution, 9.1 ml) was slowly added dropwise to a solution of m-carborane (VII-1, 1.0 g) dissolved in anhydrous THF (30 ml) at 0° C. under an argon flow and then stirred at room temperature for 5 hours. The reaction mixture was cooled again to 0° C., and a solution of 1-bromo-3-methyl-3-triethylsilyloxybutane (2.0 g) in THF (5 ml) was slowly added. The reaction mixture was stirred at room temperature for 24 hours, then poured into water and extracted with ethyl acetate. The organic phase was washed with brine and dehydrated over MgSO$_4$. The organic phase was filtered and evaporated, and the residue was purified by silica gel column chromatography (hexane) to give Compounds VII-2 (710 mg, 30%) and VII-3 (910 mg, 24%).

Compound VII-2: $^1$H-NMR (CDCl$_3$, 400 MHz) δ: 2.90 (1H, s), 2.90–1.50 (10H, br m), 2.06 (2H, m), 1.46 (2H, m), 1.15 (6H, s), 0.93 (9H, t, J=7.9 Hz), 0.55 (6H, q, J=7.9 Hz)

Compound VII-3: $^1$H-NMR (CDCl$_3$, 400 MHz) δ: 2.90–1.50 (10H, br m), 2.04 (4H, m), 1.45 (4H, m), 1.15 (12H, s), 0.93 (18H, t, J=7.9 Hz), 0.55 (12H, q, J=7.9 Hz)

Compound VII-2 (710 mg) was dissolved in a mixed solution of anhydrous benzene (4 ml) and anhydrous ether (2 ml), n-BuLi (1.60 M hexane solution, 1.4 ml) was slowly added dropwise at 0° C. under an argon flow, and then the mixture was stirred at room temperature for 1 hour. The reaction mixture was cooled again to 0° C., paraformaldehyde (99 mg, 3.09 mmol) was added, and the mixture was stirred at 0° C. to 10° C. for 5 hours. 2 N HCl was added to the reaction mixture, and the mixture was extracted with ethyl acetate. The organic phase was washed with brine and dehydrated over MgSO$_4$. The organic phase was filtered and evaporated, and the residue was purified by silica gel column chromatography (AcOEt:n-hexane=1:4) to give Compound VII-4 (662 mg, 86%).

Compound VII-4: $^1$H-NMR (CDCl$_3$, 400 MHz) δ: 3.80 (2H, d, J=7.3 Hz), 2.80–1.50 (10H, br m), 2.06 (2H, m), 1.81 (1H, t, J=7.3 Hz), 1.46 (2H, m), 1.15 (6H, s), 0.93 (9H, t, J=7.9 Hz), 0.55 (6H, q, J=7.9 Hz)

Compound VII-4 (307 mg, 0.82 mmol) was added to a suspension of pyridinium dichromate (630 mg, 1.64 mmol) in anhydrous methylene chloride (6 ml) and stirred for 54 hours. The reaction mixture was filtered through Celite and concentrated. The residue was purified by silica gel column chromatography (AcOEt:n-hexane=1:10) to give Compound VII-5 (137 mg, 45%).

Compound VII-5: $^1$H-NMR (CDCl$_3$, 400 MHz) δ: 9.04 (1H, s), 2.93–1.50 (10H, br m), 2.10 (2H, m), 1.47 (2H, m), 1.16 (6H, s), 0.93 (9H, t, J=7.9 Hz), 0.55 (6H, q, J=7.9 Hz)

Compound I-6 (251 mg, 0.44 mmol) was dissolved in THF (4 ml), n-BuLi (1.60 M hexane solution, 0.26 ml) was slowly added dropwise at −78° C. under an argon flow, and the mixture was stirred for 15 minutes. A solution of Compound VII-5 (137 mg, 0.367 mmol) in anhydrous THF (1 ml) was added dropwise to the reaction mixture. The mixture was stirred at −78° C. for 1 hour and then at room temperature for 5 hours. The reaction mixture was poured into water and extracted with ethyl acetate. The organic phase was washed with brine and dehydrated over MgSO$_4$. The organic phase was filtered and evaporated, and the residue was purified by silica gel column chromatography (AcOEt:n-hexane=1:4) to give Compound VII-7. This crude product was dissolved in a mixed solvent of methanol (4 ml) and THF (3 ml), 2 N hydrochloric acid (1 ml) was added, and the mixture was stirred at room temperature for 30 minutes. The reaction mixture was poured into water and extracted with ethyl acetate. The organic phase was washed with brine and dehydrated over MgSO$_4$. The organic phase was filtered and evaporated, and the residue was purified by silica gel column chromatography (AcOEt:n-hexane=4:1) to give Compound 16 (48 mg, 34% from VII-6).

Compound 16: $^1$H-NMR (CDCl$_3$, 400 MHz) δ: 6.49 (1H, dd, J=11.5, 15.1 Hz), 5.84 (1H, d, J=11.0 Hz), 5.60 (1H, d, J=15.0 Hz), 4.13 (2H, m), 2.66 (1H, dd, J=3.7, 13.4 Hz), 2.45 (1H, dd, J=3.6, 13.1 Hz), 2.26 (1H, dd, J=8.0, 13.5 Hz), 2.18 (1H, dd, J=6.8, 13.2 Hz), 2.07 (2H, m), 1.54 (2H, m), 1.94 (1H, m), 1.85 (1H, m), 1.18 (6H, s)

Compound VII-3 (910 mg, 1.67 mmol) was dissolved in a mixed solvent of methanol (4 ml) and THF (6 ml), 2 N hydrochloric acid (2 ml) was added, and the mixture was stirred at room temperature for 30 minutes. The reaction mixture was poured into water and extracted with ethyl acetate. The organic phase was washed with brine and dehydrated over MgSO$_4$. The organic phase was filtered and evaporated, and the residue was purified by silica gel column chromatography (AcOEt:n-hexane=1:2) to give Compound 17 (482 mg, 91%).

Compound 17: colorless prisms (CH$_2$Cl$_2$-n-hexane); mp 110–111° C.; Anal. Calcd. for C$_{12}$B$_{10}$H$_{32}$O$_2$: C, 45.54; H, 10.19. Found: C.45.52; H, 9.96. $^1$H-NMR (CDCl$_3$, 400 MHz) δ: 2.90–1.50 (10H, br m), 2.05 (4H, m), 1.51 (4H, m), 1.18 (12H, s), 1.07 (2H, s)

Example 14

Synthesis of Compound 18

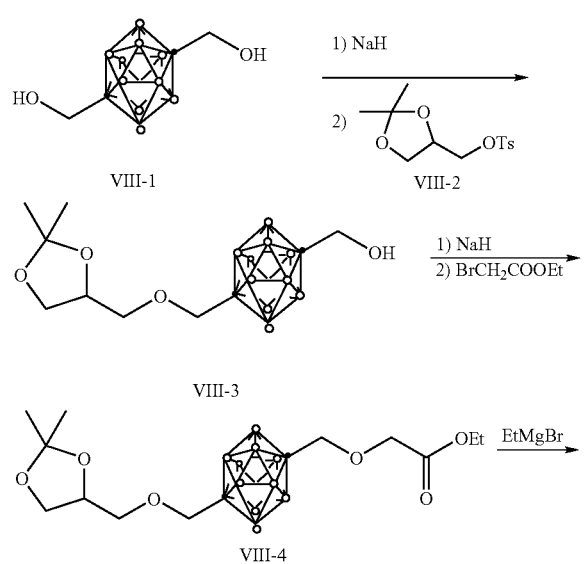

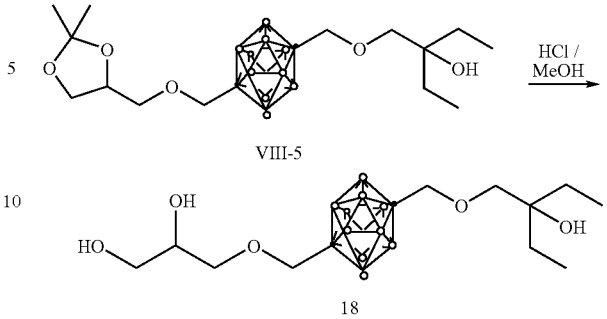

NaH (60%, 0.2242 g, 5.6 mmol) was washed with n-hexane and suspended in DMF (10 mL). A solution of Compound VIII-1 (1.0112 g, 5.0mmol) in DMF (6 mL) was added to the suspension at 0° C., and the mixture was stirred at room temperature for 1 hour. A solution of Compound VIII-2 (1.4079 g, 4.9 mmol) in DMF (4 mL) was added to this reaction mixture and stirred overnight at 90° C. The solvent was evaporated under reduced pressure, and the residue was poured into water and extracted with ethyl acetate. The organic phase was washed with water and dried over Na$_2$SO$_4$. The organic phase was filtered and evaporated, and the residue was purified by silica gel column chromatography (AcOEt:n-hexane=1:5) to give Compound VIII-3 (0.5146 g, 33%).

Compound VIII-3: $^1$H-NMR (400 MHz, CDCl$_3$) δ: 4.09–4.16 (1 H, m), 4.00 (1 H, dd, J=8.4, 6.4 Hz), 3.73 (1 H, dd, J=8.3, 6.3 Hz), 3.49 (2 H, d, J=7.3 Hz), 3.41 (1 H, dd, J=10, 5.0 Hz), 3.39 (2 H, s), 3.35 (1 H, dd, J=10, 5.7 Hz), 1.50–3.00 (10 H, brm), 1.57 (1 H, t, J=7.3 Hz), 1.39 (3 H, s), 1.34 (3 H, s)

NaH (60%, 0.0406 g, 1.0 mmol) was washed with n-hexane and suspended in DMF (2 mL). A solution of Compound VIII-3 (0.2256 g, 0.71 mmol) in DMF (3 mL) was added to the suspension at 0° C. and then stirred at room temperature for 1 hour. Ethyl bromoacetate (0.5 ml, 4.5 mmol) was added to the reaction mixture, and the mixture was stirred overnight at 50° C. The solvent was evaporated under reduced pressure, and the residue was poured into water and extracted with ethyl acetate. The organic phase was washed with water and dehydrated over Na$_2$SO$_4$. The organic phase was filtered and evaporated, and the residue was purified by silica gel column chromatography (AcOEt:n-hexane=1:7) to give Compound VIII-4 (0.1736 g, 61%). Compound VIII-4: $^1$H-NMR (400 MHz, CDCl$_3$) δ: 4.17 (2 H, q, J=7.1 Hz), 4.10–4.16 (1 H, m), 4.00 (1 H, dd, J=8.2, 6.4 Hz), 3.95 (2 H, s), 3.72 (1 H, dd, J=8.2, 6.2 Hz), 3.44 (2 H, s), 3.41 (1 H, dd, J=10, 4.9 Hz), 3.37 (2 H, s), 3.35 (1 H, dd, J=10, 5.7 Hz), 1.50–3.00 (10 H, brm), 1.38 (3 H, s), 1.33 (3 H, s), 1.26 (3 H, t, J=7.1 Hz)

Compound VIII-4 (0.0960 g, 0.24 mmol) was dissolved in THF (10 mL), a solution of ethyl magnesium bromide (0.89 M, 1.5 mL, 1.3 mmol) in THF was added at 0° C., and the mixture was stirred at room temperature for 6 hours. The reaction mixture was poured into aqueous 2 N HCl and extracted with ethyl acetate. The organic phase was dehydrated over Na$_2$SO$_4$. The organic phase was filtered and evaporated, and the residue was purified by silica gel column chromatography (AcOEt:n-hexane=1:3) to give Compound VIII-5 (0.0316 g, 32%).

Compound VIII-5: $^1$H-NMR (400 MHz, CDCl$_3$) δ: 4.10–4.16 (1 H, m), 4.00 (1 H, dd, J=8.3, 6.3 Hz), 3.73 (1 H, dd, J=8.3, 6.3 Hz), 3.40 (1 H, dd, J=10, 4.9 Hz), 3.37 (2 H, s), 3.35 (1 H, dd, J=10, 5.8 Hz), 3.31 (2 H, s), 3.15 (2 H, s), 1.50–3.00 (10 H, brm), 1.87 (1 H, s), 1.46 (4 H, m), 1.38 (3 H, s), 1.33 (3 H, s), 0.83 (6 H, t, J=7.5 Hz)

Compound VIII-5 (0.0304 g, 0.073 mmol) was dissolved in methanol (5 mL), concentrated hydrochloric acid (three drops) was added, and the mixture was stirred at room temperature for 5 hours. The reaction mixture was poured into water and extracted with methylene chloride. The organic phase was dehydrated over $Na_2SO_4$. The organic phase was filtered and evaporated, and the residue was purified by silica gel column chromatography (AcOEt) to give Compound 18 (0.0234 g, 85%).

Compound 18: $^1$H-NMR (400 MHz, CDCl3) δ: 3.78 (1 H, m), 3.67 (1 H, dd, J=11, 3.9 Hz), 3.59 (1 H, dd, J=11, 5.2 Hz), 3.41 (2 H, m), 3.36 (2 H, dd, J=8.1, 2.6 Hz), 3.32 (2 H, s), 3.15 (2 H, s), 1.50–3.00 (13 H, brm), 1.46 (4 H, m), 0.83 (6 H, t, J=7.5 Hz)

Example 15

Synthesis of Compound 19

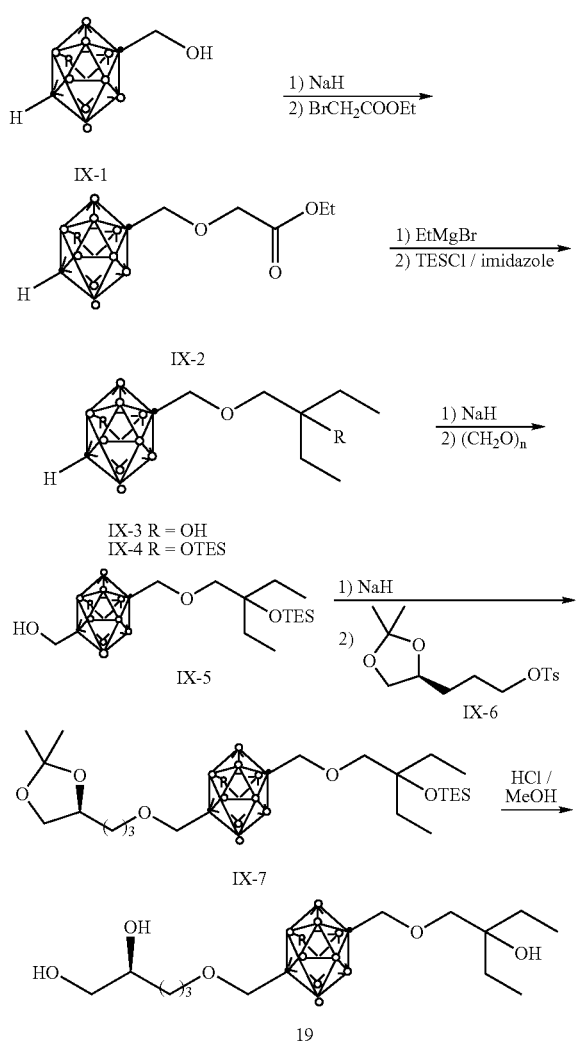

NaH (60%, 0.2981 g, 7.5 mmol) was washed with n-hexane and suspended in DMF (8 mL). A solution of Compound IX-1 (0.2256 g, 0.71 mmol) in DMF (4 mL) was added to the suspension at 0° C., and then the mixture was stirred at room temperature for 1 hour. Ethyl bromoacetate (2 ml, 18 mmol) was added to this reaction mixture and stirred overnight at room temperature. The solvent was evaporated from the reaction mixture under reduced pressure, and the residue was poured into water and extracted with ethyl acetate. The organic phase was dehydrated over $Na_2SO_4$. The organic phase was filtered and evaporated, and the residue was purified by silica gel column chromatography (AcOEt:n-hexane=1:7) to give Compound IX-2 (0.9415 g, 64%).

Compound IX-2: $^1$H-NMR (400 MHz, CDCl$_3$) δ: 4.17 (2 H, q, J=7.1 Hz), 3.96 (2 H, s), 3.43 (2 H, s), 1.50–3.00 (11 H, brm), 1.26 (3 H, t, J=7.1 Hz)

Compound IX-2 (0.5242 g, 2.0 mmol) was dissolved in THF (30 mL), a solution of ethyl magnesium bromide (0.89 M, 7.0 mL, 6.2 mmol) in THF was added at 0° C., and the mixture was stirred at room temperature for 5 hours. The reaction mixture was poured into aqueous 2 N HCl and extracted with ethyl acetate. The organic phase was dehydrated over $Na_2SO_4$. The organic phase was filtered and evaporated, and the residue was purified by silica gel column chromatography (AcOEt:n-hexane=1:6) to give Compound IX-3 (0.3881 g, 70%).

Compound IX-3: $^1$H-NMR (400 MHz, CDCl$_3$) δ: 3.30 (2 H, s), 3.15 (2 H, s), 1.50–3.00 (11 H, brm), 1.46 (4 H, m), 0.83 (6 H, t, J=7.5 Hz)

Compound IX-3 (0.4171 g, 1.5 mmol) was dissolved in 1,2-dichloroethane (5 mL), 2,6-lutidine (0.3232 g, 3.0 mmol) and trifluoromethanesulfonic acid triethylsilyl ester (0.4873 g, 1.8 mmol) was added at 0° C., and the mixture was stirred overnight at room temperature. The reaction mixture was poured into aqueous 2 N HCl and extracted with methylene chloride. The organic phase was dehydrated over $Na_2SO_4$. The organic phase was filtered and evaporated, and the residue was purified by silica gel column chromatography (n-hexane) to give Compound IX-4 (0.3876 g, 66%).

Compound IX-4: $^1$H-NMR (400 MHz, CDCl$_3$) δ: 3.24 (2 H, s), 3.10 (2 H, s), 1.50–3.00 (11 H, brm), 1.45 (4 H, m), 0.91 (9 H, t, J=7.9 Hz), 0.80 (6 H, t, J=7.4 Hz), 0.53 (6 H, q, J=7.9 Hz)

n-BuLi (1.59 M in hexane, 0.8 mL, 1.27 mmol) was added to a solution (6 mL) of Compound IX-4 (0.3866 g, 1.00 mmol) in benzene and ether (2:1) at 0° C. under argon atmosphere, and the mixture was stirred for 1.5 hours at room temperature. Paraformaldehyde (94%, 0.0518 g, 1.62 mmol) was added, and the mixture was stirred for 4 days out at room temperature. Aqueous 2 N HCl was added to the reaction mixture and extracted with ethyl acetate. The organic phase was washed with brine and dehydrated over $Na_2SO_4$. The organic phase was filtered and evaporated to give Compound IX-5 (0.4152 g, quant).

Compound IX-5: $^1$H-NMR (400 MHz, CDCl$_3$) δ: 3.49 (2 H, s), 3.27 (2 H, s), 3.11 (2 H, s), 1.50–3.00 (11 H, brm), 1.45 (4 H, m), 0.91 (9 H, t, J=8.0 Hz), 0.80 (6 H, t, J=7.4 Hz), 0.53 (6 H, q, J=7.9 Hz)

NaH (60%, 0.0196 g, 0.49 mmol) was washed with n-hexane and suspended in DMF (1 mL). A solution of Compound IX-5 (0.1009 g, 0.24 mmol) in DMF (2 mL) was added to the suspension at 0° C., and the mixture was stirred at room temperature for 1 hour. A solution of Compound IX-6 (0.0753 g, 0.24 mmol) in DMF (2 mL) was added to this reaction mixture, and the mixture was stirred overnight at room temperature. The solvent was evaporated from the reaction mixture under reduced pressure, and the residue was poured into water and extracted with ethyl acetate. The organic phase was washed with water and dehydrated over Na$_2$SO$_4$. The organic phase was filtered and evaporated, and the residue was purified by silica gel column chromatography (AcOEt:n-hexane=1:7) to give Compound IX-7 (0.0723 g, 54%).

Compound IX-7: $^1$H-NMR (400 MHz, CDCl$_3$) δ: 4.06 (1 H, m), 4.03 (1 H, dd, J=7.5, 5.9 Hz), 3.50 (1H, t, J=7.2 Hz), 3.31 (2 H, m), 3.28 (2 H, s), 3.26 (2 H, s), 3.10 (2 H, s), 1.50–3.00 (10 H, brm), 1.59 (2 H, m), 1.46 (4 H, m), 1.40 (3 H, s), 1.35 (3 H, s), 0.91 (9 H, t, J=7.9 Hz), 0.79 (6 H, t, J 7.5 Hz), 0.53 (6 H, q, J=7.9 Hz)

Compound IX-7 (0.0723 g, 0.13 mmol) was dissolved in methanol (4 mL), aqueous 2 N HCl (1 mL) was added, and the mixture was stirred at room temperature for 1 hour. The reaction mixture was poured into water and extracted with ethyl acetate. The organic phase was washed with brine and dehydrated over Na$_2$SO$_4$. The organic phase was filtered and evaporated, and the residue was purified by silica gel column chromatography (AcOEt) to give Compound 19 (0.0403 g, 77%).

Compound 19: $^1$H-NMR (400 MHz, CDCl$_3$) δ: 3.69 (1 H, m), 3.63 (1 H, m), 3.44 (1 H, m), 3.34 (2 H, m), 3.32 (2 H, s), 3.30 (2 H, s), 3.15 (2 H, s), 1.50–3.00 (10 H, brm), 2.43 (1H, d, J=4.0 Hz), 1.90 (1H, dd, J=6.6, 4.9 Hz), 1.87 (1 H, s), 1.62 (2 H, m), 1.46 (4 H, m), 0.83 (6 H, t, J=7.5 Hz)

Test Example 1

Test for Induction of Cell Differentiation in HL-60 Cells

Cell differentiation-inducing action was examined for each of the compounds obtained in the examples alone or with the coexistence of 1×10$^{-8}$ M1α,25-dihydroxyvitamin D$_3$ (VD3). According to the method described in Japanese Patent Unexamined Publication (Kokai) No. 61-76440, cell differentiation of promyelocytic leukemia strain HL-60 into granulocytic series was determined based on morphological change and measurement of ability to reduce nitroblue tetrazolium (NBT). The values in the table indicate ratios (%) of differentiated cells calculated from the NBT reducing ability, and the row represented by "VD3" indicates the results obtained by using vitamin D$_3$.

| Compound | Concentration (Log Concentration, M) | | | | | | | | |
|---|---|---|---|---|---|---|---|---|---|
| | −9 | −8 | −7 | −6 | −5 | None | −7 | −6 | −5 |
| VD3 | 7 | 41 | 75 | | | | | | |
| 1 | | | 4 | 3 | 7 | 21 | 51 | 73 | 72 |
| 2 | | 1 | 7 | 31 | 81 | | | | |
| 3 | | 2 | 2 | 47 | 86 | | | | |
| 4 | | 2 | 1 | 44 | 73 | | | | |
| 5 | | 1 | 1 | 27 | 47 | | | | |
| 6 | | 2 | 1 | 3 | 66 | | | | |
| 7 | | 1 | 2 | 26 | 81 | | | | |
| 8 | 2 | 10 | 55 | 72 | 81 | | | | |
| 9 | 1 | 5 | 42 | 72 | 75 | | | | |
| 10 | 0.5 | 0.5 | 0.5 | 2 | 34 | | | | |
| 11 | 1 | 12 | 60 | 66 | 47 | | | | |
| 12 | 1 | 0.5 | 0.5 | 2 | 40 | | | | |
| 13 | | | 1 | 2 | 4 | 21 | 34 | 49 | 41 |
| 14 | | | 3 | 2 | 5 | 21 | 39 | 41 | 78 |
| 15 | | | 3 | 1 | 1 | 21 | 31 | 38 | 51 |
| 16 | | | 2 | 2 | 5 | | | | |
| 17 | | | 2 | 2 | 6 | 21 | 39 | 70 | 41 |
| 18 | | 2 | 0.5 | 2 | 3 | 43 | 55 | 63 | 73 |
| 19 | | 2 | 2 | 10 | 58 | 43 | 59 | 75 | 91 |

INDUSTRIAL APPLICABILITY

The medicaments comprising the compounds represented by the aforementioned formula (I) or physiologically acceptable salts thereof as an active ingredient are useful as agents having vitamin D actions or agents for enhancing vitamin D actions.

What is claimed is:

1. A compound represented by the following general formula (I):

$$R^1\text{—}X\text{—}R^2 \qquad (I)$$

wherein R$^1$ represents a hydroxy-substituted alkyl group, X represents a dicarba-closo-dodecaborane-diyl group; R$^2$ represents a hydroxy-substituted alkyl group or a hydroxy-substituted alkoxyalkyl group, or a salt thereof; and R$^1$ and R$^2$ are bound to carbon atoms of said dicarba-closo-dodecaborane-diyl group.

2. The compound or a salt thereof according to claim 1, wherein the hydroxy-substituted alkenyl group represented by R$^1$ is a group represented by the following formula

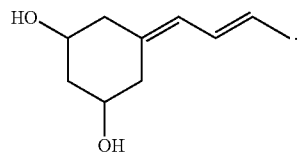

3. A medicament composition comprising the compound or a physiologically acceptable salt thereof according to claim 1 as an active ingredient with one or more pharmaceutical additives.

4. The medicament composition according to claim 3, which has vitamin D actions or enhances vitamin D actions.

5. A medicament composition comprising the compound or a physiologically acceptable salt thereof according to claim 2 as an active ingredient with one or more pharmaceutical additives.

6. The medicament composition according to claim 5, which has vitamin D actions or enhances vitamin D actions.

7. A method of exerting vitamin D action comprising administering to a patient an effective amount to exert vitamin D action of a compound represented by the following general formula (I) or a physiologically acceptable salt thereof:

$$R^1\text{—}X\text{—}R^2 \qquad (I)$$

wherein R$^1$ represents a hydroxy-substituted alkyl group, a hydroxy-substituted alkenyl group, a hydroxy-substituted arylalkyl group wherein said arylalkyl group may have a substituent on the aryl ring, or a hydroxy-substituted arylalkenyl group wherein said arylalkenyl group may have a substituent on the aryl ring; X represents a dicarba-closo-dodecaborane-diyl group; R$^2$ represents a hydroxy-substituted alkyl group or a hydroxy-substituted alkoxyalkyl group, or a salt thereof; and R$^1$ and R$^2$ are bound to carbon atoms of said dicarba-closo-dodecaborane-diyl group.

8. The method according to claim 7, wherein R$^1$ represents a hydroxy-substituted alkenyl group.

9. The method according to claim 8, wherein the hydroxy-substituted alkenyl group represented by R$^1$ is a group represented by the following formula

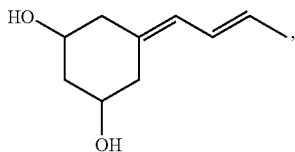

10. The method according to claim 7, wherein the compound represented by the following general formula (I) or a physiologically acceptable salt thereof comprises an active ingredient of a composition.

11. The method according to claim 8, wherein the compound represented by the following general formula (I) or a physiologically acceptable salt thereof comprises an active ingredient of a composition.

12. The method according to claim 9, wherein the compound represented by the following general formula (I) or a physiologically acceptable salt thereof comprises an active ingredient of a composition.

13. A method of enhancing vitamin D action comprising administering to a patient an effective amount to enhance vitamin D action of a compound represented by the following general formula (I) or a physiologically acceptable salt thereof:

$$R^1—X—R^2 \qquad (I)$$

wherein $R^1$ represents a hydroxy-substituted alkyl group, a hydroxy-substituted alkenyl group, a hydroxy-substituted arylalkyl group wherein said arylalkyl group may have a substituent on the aryl ring, or a hydroxy-substituted arylalkenyl group wherein said arylalkenyl group may have a substituent on the aryl ring; X represents a dicarba-closo-dodecaborane-diyl group; $R^2$ represents a hydroxy-substituted alkyl group or a hydroxy-substituted alkoxyalkyl group, or a salt thereof; and $R^1$ and $R^2$ are bound to carbon atoms of said dicarba-closo-dodecaborane-diyl group.

14. The method according to claim 13, wherein $R^1$ represents a hydroxy-substituted alkenyl group.

15. The method according to claim 14, wherein the hydroxy-substituted alkenyl group represented by $R^1$ is a group represented by the following formula

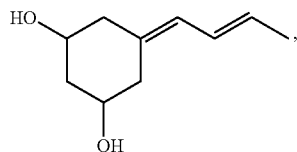

16. The method according to claim 13, wherein the compound represented by the following general formula (I) or a physiologically acceptable salt thereof comprises an active ingredient of a composition.

17. The method according to claim 14, wherein the compound represented by the following general formula (I) or a physiologically acceptable salt thereof comprises an active ingredient of a composition.

18. The method according to claim 15, wherein the compound represented by the following general formula (I) or a physiologically acceptable salt thereof comprises an active ingredient of a composition.

* * * * *